(12) United States Patent
Cesura et al.

(10) Patent No.: US 6,818,774 B2
(45) Date of Patent: Nov. 16, 2004

(54) ISOQUINOLINE DERIVATIVES

(75) Inventors: Andrea Cesura, Crans-pres-Celigny (CH); Rosa Maria Rodriguez Sarmiento, Basel (CH); Michelangelo Scalone, Birsfelden (CH); Andrew William Thomas, Birsfelden (CH); Rene Wyler, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/417,378

(22) Filed: Apr. 16, 2003

(65) Prior Publication Data
US 2003/0225122 A1 Dec. 4, 2003

(30) Foreign Application Priority Data
Apr. 26, 2002 (EP) .............................. 02009253

(51) Int. Cl.$^7$ .................. C07D 217/22; C07D 217/02; C07D 401/00; A61K 31/44; A61K 31/47
(52) U.S. Cl. .................... 546/196; 546/142; 546/143; 546/147; 546/141; 514/307; 514/309; 514/310
(58) Field of Search ................. 546/196, 142, 546/143, 147, 141; 514/307, 309, 310

(56) References Cited

U.S. PATENT DOCUMENTS

| 5,731,324 | A | * | 3/1998 | Fisher | |
|---|---|---|---|---|---|
| 6,020,362 | A | * | 2/2000 | Fisher | |
| 6,137,002 | A | * | 10/2000 | Fisher et al. | 562/440 |
| 6,448,269 | B1 | * | 9/2002 | Fisher et al. | 514/320 |
| 6,472,405 | B1 | * | 10/2002 | Fisher | |

FOREIGN PATENT DOCUMENTS

| EP | 0635492 | 1/1995 |
|---|---|---|
| WO | WO 9622288 | 7/1996 |
| WO | WO 96/40095 | 12/1996 |
| WO | WO 97/33572 | 9/1997 |
| WO | WO 01/34172 | 5/2001 |

OTHER PUBLICATIONS

Fisher et al, Bioorganic & Medicinal Chemistry Letters, vol. 7, No. 19 (1997) p. 2537–2542.
Kalgutkar et al, Medicinal Research Reviews, vol. 15, No. 4, (1995) pp. 325–388.
Foley et al, Elsevier Science, vol. 6, No. 1 (2000) pp. 25–47 (XP00087269).
Bach et al., Proc. Natl. Acad. Sci. USA, 1988, vol. 85, pp. 4934–4938.
Cesura & Pletscher, Prog. Drug Research, 1992, vol. 38, pp. 171–297.
Fowler, et al., J. Neural. Trans., 1980, vol. 49, pp. 1–20.
Benedetti et al., Biochem. Pharmacol., 1989, vol. 38, pp. 555–561.
Saura et al., Neuroscience, 1996, vol. 70, pp. 755–744.
Bentué–Ferrer et al., CNS Drugs, 1996, vol. 6, pp. 217–236.
Gardner et al., J. Clin. Psychiatry, 1996, vol. 57, pp. 99–104.
Cahn et al., Angew Chem. 1966, vol. 5, No. 4, pp. 385–415.
Cahn & Ingold, J. Chem. Soc. (London), 1951, pp. 612–622.
Cahn et al., Experientia, 1956, vol. 12, pp. 81–124.
Cahn, J. Chem. Educ. 1964, vol. 41, pp. 116–125.
Schlaeger & Christensen, Cytotechnology, 1999, vol. 30, pp. 71–83.
Zhou & Panchuk–Voloshina, Analytical Biochemistry, 1997, vol. 253, pp. 169–174.

* cited by examiner

Primary Examiner—D. Margaret Seaman
(74) Attorney, Agent, or Firm—George W. Johnston; Patricia S. Rocha-Tramaloni; Kimberly J. Prior

(57) ABSTRACT

Disclosed are isoquinolino derivatives of the formula

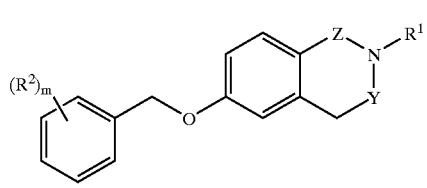

wherein Y is >C=O or —CH$_2$—, Z is >C=O or —CH$_2$—, and R$^1$, R$^2$ and m are as defined herein as well as the pharmaceutically acceptable salts thereof. These compounds are MAO-B selective inhibitors useful, inter alia, in the treatment of Alzheimer's disease and/or senile dementia.

37 Claims, No Drawings

ISOQUINOLINE DERIVATIVES

SUMMARY OF THE INVENTION

This invention relates to novel isoquinolino derivatives that are selective monoamine oxidase B inhibitors. These compounds are useful in the treatment or control of Alzheimer's disease and dementia. This invention also relates to pharmaceutical compositions containing these compounds and to methods of treating Alzheimer's disease and dementia using these compounds.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes (A. W. Bach et al., *Proc. Natl. Acad. Sci. USA* 1988, 85, 4934–4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, Prog. Drug Research 1992, 38, 171–297). Brain MAO-B activity appears to increase with age. This increase has been attributed to the gliosis associated with aging (C. J. Fowler et al., *J. Neural. Transm.* 1980, 49, 1–20). Additionally, MAO-B activity is significantly higher in the brains of patients with Alzheimer's disease (P. Dostert et al., *Biochem. Pharmacol.* 1989, 38, 555–561) and it has been found to be highly expressed in astrocytes around senile plaques (Saura et al., *Neuroscience* 1994, 70, 755–774). In this context, since oxidative deamination of primary monoamines by MAO produces $NH_3$, aldehydes and $H_2O_2$, agents with established or potential toxicity, it is believed that selective MAO-B inhibitors are useful for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in *CNS Drugs* 1996, 6, 217–236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99–104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$C_1$–$C_6$-alkyl" ("lower alkyl") used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

The term "halogen" denotes fluorine, chlorine, bromine and iodine. "Halogen-($C_1$–$C_6$)-alkyl" or "halogen-($C_1$–$C_6$)-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. "Halogenalkoxy" includes trifluoromethyloxy.

"$C_1$–$C_6$-Alkoxy" means the residue —O—R, wherein R is a lower alkyl residue as defined herein. Examples of alkoxy radicals include, but are not limited to, methoxy, ethoxy, isopropoxy, and the like.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, 2,2,2-trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

"Chiral compound" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". When chiral centers are present, the stereoisomers may be characterized by the absolute configuration (R or S) of the chiral centers. Absolute configuration refers to the arrangement in space of the substituents attached to a chiral center. The substituents attached to a chiral center under consideration are ranked in accordance with the *Sequence Rule* of Cahn, Ingold and Prelog. (Cahn et al.,*Angew. Chem.*, 1966, 78, 413; Cahn and Ingold *J. Chem. Soc.* (London), 1951, 612; Cahn et al., *Experientia*, 1956, 12, 81; Cahn, *J., Chem. Educ.,* 1964, 41, 116).

"Pure" means at least about 80 mole percent, more preferably at least about 90 mole percent, and most preferably at least about 95 mole percent of the desired enantiomer or stereoisomer is present.

In one embodiment, the present invention relates to a compound of formula I,

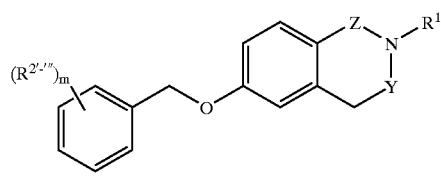

I wherein
Y is >C=O or —CH$_2$—;
Z is >C=O or —CH$_2$—;
R$^1$ is hydrogen or is a group of formula

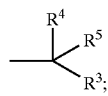

(a)

R$^{2^{1-111}}$ each R$^2$ is independently selected from halogen, halogen-(C$_1$–C$_6$)-alkyl, cyano, C$_1$–C$_6$-alkoxy or halogen-(C$_1$–C$_6$)-alkoxy,
R$^3$ is selected from —(CH$_2$)$_n$—CO—NR$^6$R$^7$,
—(CH$_2$)$_n$—COOR$^8$,
—CHR$^9$—COOR$^8$,
—(CH$_2$)$_n$—CN,
—(CH$_2$)$_p$—OR$^8$,
—(CH$_2$)$_n$—NR$^6$R$^7$,
—(CH$_2$)$_n$—CF$_3$,
—(CH$_2$)$_n$—NH—COR$^9$'
—(CH$_2$)$_n$—NH—COOR$^8$,
—(CH$_2$)$_n$-tetrahydrofuranyl,
—(CH$_2$)$_p$—hu 8,
—(CH$_2$)$_p$—SO—R$^9$, or
—(CH$_2$)$_p$—CS—NR$^5$R$^6$;

R$^4$ is hydrogen, C$_1$–C$_6$-alkyl, —(CH$_2$)$_p$—OR$^8$, —(CH$_2$)$_p$—SR$^8$, or benzyl;
R$^5$ is hydrogen, C$_1$–C$_6$-alkyl, —(CH$_2$)$_p$—OR$^8$, —(CH$_2$)$_p$—SR$^8$, or benzyl;
R$^6$ and R$^7$ are each independently selected from hydrogen or C$_1$–C$_6$-alkyl;
R$^8$ is hydrogen or C$_1$–C$_6$-alkyl;
R$^9$ is C$_1$–C$_6$-alkyl;
m is 1, 2 or 3;
n is 0, 1 or 2; and
p is 1 or 2;
or the pharmaceutically acceptable salts thereof.

Another embodiment of the present invention relates to pharmaceutical compositions containing a therapeutically effective amount of a compound of formula I, or a pharmaceutically acceptable salt thereof, and a pharmaceutically acceptable, inert carrier or excipient.

In another embodiment, the invention relates to a method of treating, controlling or preventing a disease mediated by MAO-B inhibition, including Alzheimer's disease and dementia, comprising administering to a patient in need of such therapy a therapeutically effective amount of a compound of formula I, or a pharmaceutically acceptable salt thereof.

Compounds of formula I wherein at least one of Y or Z is >C=O are preferred.

Also preferred are compounds of formula 1, wherein either R$^4$ or R$^5$ is C$_1$–C$_6$-alkyl.

Especially preferred are those compounds, wherein either R$^4$ or R$^5$ is methyl.

Further preferred compounds of formula I are those, in which R$^1$ is a group of formula

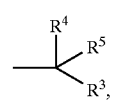

(a)

wherein R$^3$, R$^4$ and R$^5$ have the above meanings.

Especially preferred are compounds of formula I having the formula

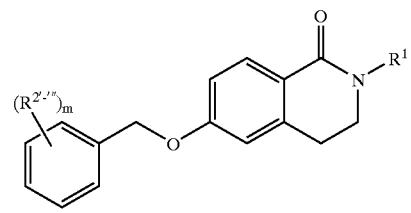

I-A wherein
R$^1$ is hydrogen or is a group of formula

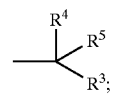

(a)

R$^{2^{1-111}}$ each R$^2$ is independently selected from halogen, halogen-(C$_1$–C$_6$)-alkyl, cyano, C$_1$–C$_6$-alkoxy or halogen-(C$_1$–C$_6$)-alkoxy,
R$^3$ is selected from —(CH$_2$)$_n$—CO—NR$^6$R$^7$,
—(CH$_2$)$_n$—COOR$^8$,
—CHR$^9$—COOR$^8$, —$(CH_2)_n$—CN,
—$(CH_2)_p$—$OR^8$,
—$(CH_2)_n$—$NR^6R^7$,
—$(CH_2)_n$—$CF_3$,
—$(CH_2)_n$—NH—$COR^9$,
—$(CH_2)_n$—NH—$COOR^8$,
—$(CH_2)_n$-tetrahydrofuranyl,
—$(CH_2)_p$—$SR^8$,
—$(CH_2)_p$—SO—$R^9$, or
—$(CH_2)_p$—CS—$NR^5R^6$;
$R^4$ is hydrogen, $C_1$–$C_6$-alkyl, —$(CH_2)_p$—$OR^8$, —$(CH_2)_p$—$SR^8$, or benzyl;
$R^5$ is hydrogen, $C_1$–$C_6$-alkyl, —$(CH_2)_p$—$OR^8$, —$(CH_2)_p$—$SR^8$, or benzyl;
$R^6$ and $R^7$ are independently selected from hydrogen or $C_1$–$C_6$-alkyl;
$R^8$ is hydrogen or $C_1$–$C_6$-alkyl;
$R^9$ is $C_1$–$C_6$-alkyl;
m is 1, 2 or 3;
n is 0, 1 or 2; and
p is 1 or 2;
or the pharmaceutically acceptable salts thereof.

Most preferred are compounds of formula I-A, wherein $R^1$ is a group of formula (a); $R^3$ is selected from —$(CH_2)_n$—CO—$NR^6R^7$, —$(CH_2)_n$—$COOR^8$)—$(CH_2)_n$—CN or —$(CH_2)_p$—$OR^8$; $R^6$ and $R^7$ are each independently selected from hydrogen or $C_1$–$C_6$-alkyl; $R^8$ is hydrogen or $C_1$–$C_6$-alkyl; n is 0, 1 or 2; and p is 1 or 2. Particularly preferred within this group of compounds of formula I-A are those wherein $R^3$ is —$(CH_2)_n$—CO—$NR^6R^7$; $R^6$ and $R^7$ are each independently selected from hydrogen or $C_1$–$C_6$-alkyl; and n is 0, 1 or 2.

Examples of foregoing preferred compounds include:
2-[6-(3-fluoro-benzyloxy)-1-oxo-3,4-dihydro-1H-isoquinolin-2-yl]-acetamide,
2-[6-(3-fluoro-benzyloxy)-1-oxo-3,4-dihydro-1H-isoquinolin-2-yl]-propionamide
2-[6-(4-fluoro-benzyloxy)-1-oxo-3,4-dihydro-1H-isoquinolin-2-yl]-propionamide,
2-[6-(3,4-difluoro-benzyloxy)-1-oxo-3,4-dihydro-1H-isoquinolin-2-yl]-propionamide, and
2-[6-(3-fluoro-benzyloxy)-1-oxo-3,4-dihydro-1H-isoquinolin-2-yl]-propionamide.

Another preferred embodiment of the invention includes compounds of formula I wherein $R^4$ and $R^5$ have different meanings. These compounds have a chiral center and therefore exist in racemic form or in the two enantiomeric forms. Especially preferred are the pure enantiomers.

Examples of such enantiomeric compounds are compounds of formula I-A, wherein $R^3$ is —$(CH_2)_n$—CO—$NR^6R^7$; $R^6$ and $R^7$ are each independently selected from hydrogen or $C_1$–$C_6$-alkyl; and n is 0, 1 or 2. Specifically, examples of such compounds include:
2-(R)-[6-(3-fluoro-benzyloxy)-1-oxo-3,4-dihydro-1H-isoquinolin-2-yl)-propionamide,
2-(R)-[6-(4-fluoro-benzyloxy)-1-oxo-3,4-dihydro-1H-isoquinolin-2-yl]-propionamide,
2-(S)-[6-(4-fluoro-benzyloxy)-1-oxo-3,4-dihydro-1H-isoquinolin-2-yl]-propionamide,
2-(R)-[6-(2,6-difluoro-benzyloxy)-1-oxo-3,4-dihydro-1H-isoquinolin-2-yl-propionamide, and
2-(S)-[6-(4-fluoro-benzyloxy)-1-oxo-3,4-dihydro-1H-isoquinolin-2-yl]-3-hydroxy-propionamide.

Also preferred are compounds of formula

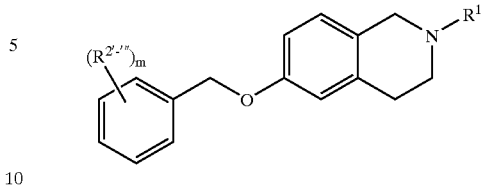

I-B wherein
$R^1$ is hydrogen or is a group of formula

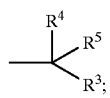

(a)

$R^{2\text{-}\text{\tiny{III}}}$ each $R^2$ is independently selected from halogen, halogen-($C_1$–$C_6$)-alkyl, cyano, $C_1$–$C_6$-alkoxy or halogen-($C_1$–$C_6$)-alkoxy,
$R^3$ is selected from —$(C_2)_n$—CO—$NR^6R^7$,
—$(CH_2)_n$—$COOR^8$,
—$CHR^9$—$COOR^8$,
—$(CH_2)_n$—CN,
—$(CH_2)_p$—$OR^8$,
—$(CH_2)_n$—$NR^6R^7$,
—$(CH_2)_n$—$CF_3$,
—$(CH_2)_n$—NH—$COR^9$,
—$(CH_2)_n$—NH—$COOR^8$,
—$(CH_2)_n$-tetrahydrofuranyl,
—$(CH_2)_p$—$SR^8$,
—$(CH_2)_p$—SO—$R^9$, or
—$(CH_2)_n$—CS—$NR^5R^6$;
$R^4$ is hydrogen, $C_1$–$C_6$-alkyl, —$(CH_2)_p$—$OR^8$, —$(CH_2)P$—$SR^8$, or benzyl;
$R^5$ is hydrogen, $C_1$–$C_6$-alkyl, —$(CH_2)P$—$OR^8$, —$(CH_2)_p$—$SR^8$, or benzyl;
$R^6$ and $R^7$ are each independently selected from hydrogen or $C_1$–$C_6$-alkyl;
$R^8$ is hydrogen or $C_1$–$C_6$-alkyl;
$R^9$ is $C_1$–$C_6$-alkyl;
m is 1, 2 or 3;
n is 0, 1 or 2; and
p is 1 or 2;
or the pharmaceutically acceptable salts thereof Preferred compounds of formula I-B are those wherein $R^1$ is a group of formula (a); $R^3$ is selected from —$(CH_2)_n$—CO—$NR^6R^7$, —$(CH_2)_n$—$COOR^8$, —$CHR^9$—$COOR^8$, —$(CH_2)_n$—CN, —$(CH_2)_n$—$CF_3$, —$(CH_2)_p$—$OR^8$ or —$(CH_2)_n$-tetrahydrofuranyl; $R^6$ and $R^7$ are each independently selected from hydrogen or $C_1$–$C_6$-alkyl; $R^8$ is hydrogen or $C_1$–$C_6$-alkyl; n is 0, 1 or 2; and p is 1 or 2. Especially preferred within this group of compounds of formula I-B are those compounds wherein $R^3$ is —$(CH_2)_n$—CO—$NR^6R^7$; $R^6$ and $R^7$ are each independently selected from hydrogen or $C_1$–$C_6$-alkyl; and n is 0, 1 or 2.

Examples of preferred compounds according to formula I-B include:
2-[6-(3-fluoro-benzyloxy)-3,4-dihydro-1H-isoquinolin-2-yl]-propionamide,
2-[6-(4-fluoro-benzyloxy)-3,4-dihydro-1H-isoquinolin-2-yl]-acetamide,
2-[6-(3-fluoro-benzyloxy)-3,4-dihydro-1H-isoquinolin-2-yl]-acetamide, and 2-[6-(4-fluoro-benzyloxy)-3,4-dihydro-1H-isoquinolin-2-yl]-propionamide.

Another especially preferred group of compounds of formula I-B are those wherein $R^3$ is —$(CH_2)_p$—$OR^8$; $R^8$ is $C_1$–$C_6$-alkyl; and p is 1 or 2.

The present invention is also concerned with compounds of formula

I-C wherein
$R^1$ is hydrogen or is a group of formula (a)

$R^{2\text{-}111}$ each $R^2$ is independently selected from halogen, halogen-($C_1$–$C_6$)-alkyl, cyano, $C_1$–$C_6$-alkoxy or halogen-($C_1$–$C_6$)-alkoxy,
$R^3$ is selected from —$(CH_2)_n$—CO—$NR^6R^7$,
  —$(CH_2)_n$—$COOR^8$,
  —$CHR^9$—$COOR^8$,
  —$(CH_2)_n$—CN,
  —$(CH_2)_p$—$OR^8$,
  —$(CH_2)_n$—$NR^6R^7$,
  —$(CH_2)_n$—$CF_3$,
  —$(CH_2)_n$—NH—$COR^9$,
  —$(CH_2)_n$—NH—$COOR^8$,
  —$(CH_2)_n$-tetrahydrofuranyl,
  —$(CH_2)_p$—$SR^8$,
  —$(CH_2)_p$—SO—$R^9$, or
  —$(CH_2)_n$—CS—$NR^5R^6$;
$R^4$ is hydrogen, $C_1$–$C_6$-alkyl, —$(CH_2)_p$—$OR^8$, —$(CH_2)_n$—$SR^8$, or benzyl;
$R^5$ is hydrogen, $C_1$–$C_6$-alkyl, —$(CH_2)_p$—$OR^8$, —$(CH_2)_p$—$SR^8$, or benzyl;
$R^6$ and $R^7$ are each independently selected from hydrogen or $C_1$–$C_6$-alkyl;
$R^8$ is hydrogen or $C_1$–$C_6$-alkyl;
$R^9$ is $C_1$–$C_6$-alkyl;
m is 1, 2 or 3;
n is 0, 1 or 2; and
p is 1 or 2;
or the pharmaceutically acceptable salts thereof.

Preferred compounds of formula I-C are those wherein $R^1$ is a group of formula (a); $R^3$ is —$(CH_2)_n$—CO—$NR^6R^7$, —$(CH_2)_n$—$COOR^8$, —$(CH_2)_n$—CN or —$(CH_2)_p$—$OR^8$; $R^6$ and $R^7$ are each independently selected from hydrogen or $C_1$–$C_6$-alkyl; $R^8$ is hydrogen or $C_1$–$C_6$-alkyl n is 0, 1 or 2; and p is 1 or 2. Especially preferred within this group of compounds of formula I-C are those, wherein $R^3$ is —$(CH_2)_n$—CO—$NR^6R^7$; $R^6$ and $R^7$ are each independently selected from hydrogen or $C_1$–$C_6$-alkyl; and n is 0, 1 or 2.

Examples of preferred compounds of formula I-C include:
2-(R)-[6-(4-fluoro-benzyloxy)-1,3-dioxo-3,4-dihydro-1H-isoquinolin-2-yl]-propionamide, and
2-(S)-[6-(4-fluoro-benzyloxy)-1,3-dioxo-3,4-dihydro-1H-isoquinolin-2-yl]-propionamide.

The present invention is also directed to compounds of formula I

I-D wherein
$R^1$ is hydrogen or is a group of formula (a)

$R^{2\text{-}111}$ each $R^2$ is independently selected from halogen, halogen-($C_1$–$C_6$)-alkyl, cyano, CS—$C_6$-alkoxy or halogen-($C_1$–$C_6$)-alkoxy,
$R^3$ is selected from —$(CH_2)_n$—CO—$NR^6R^7$,
  —$(CH_2)_n$—$COOR^8$,
  —$CHR^9$—$COOR^8$,
  —$(CH_2)_n$—CN,
  —$(CH_2)_p$—$OR^8$,
  —$(CH_2)_n$—$NR^6R^7$,
  —$(CH_2)_n$—$CF_3$,
  —$(CH_2)_n$—NH—$COR^9$,
  —$(CH_2)_n$—NH—$COOR^8$,
  —$(CH_2)_n$-tetrahydrofuranyl,
  —$(CH_2)_p$—$SR^8$,
  —$(CH_2)_p$—SO—$R^9$, or
  —$(CH_2)_n$—CS—$NR^5R^6$;
$R^4$ is hydrogen, $C_1$–$C_6$-allyl, —$(CH_2)_p$—$OR^8$, —$(CH_2)_p$—$SR^8$, or benzyl;
$R^5$ is hydrogen, $C_1$–$C_6$-alkyl, —$(CH_2)P$—$OR^8$, —$(CH_2)_p$—$SR^8$, or benzyl;
$R^6$ and $R^7$ are each independently selected from hydrogen or $C_1$–$C_6$-alkyl;
$R^8$ is hydrogen or $C_1$–$C_6$-alkyl;
$R^9$ is $C_1$–$C_6$-alkyl;
m is 1, 2 or 3;
n is 0, 1 or 2; and
p is 1 or 2;
or the pharmaceutically acceptable salts thereof.

Preferred compounds of formula I-D are those wherein $R^1$ is a group of formula (a); $R^3$ is $(CH_2)_n$—CO—$NR^6R^7$, —$(CH_2)_n$—$COOR^8$, —$(CH_2)_n$—CN or —$(CH_2)_p$—$OR^8$; $R^6$ and $R^7$ are each independently selected from hydrogen or $C_1$–$C_6$-alkyl; RB is hydrogen or $C_1$–$C_6$-alkyl; n is 0, 1 or 2; and p is 1 or 2. Especially preferred within this group of compounds of formula I-D are those wherein $R^3$ is —$(CH_2)_n$—CO—$NR^6R^7$; $R^6$ and $R^7$ are each independently selected from hydrogen or $C_1$–$C_6$-alkyl; and n is 0, 1 or 2.

Examples of preferred compounds of formula I-D include:
2-(S)-[6-(4-fluoro-benzyloxy)-3-oxo-3,4-dihydro-1H-isoquinolin-2-yl]-propionamide, and 2-(R)-16-(4-fluoro-benzyloxy)-3-oxo-3,4-dihydro-1H-isoquinolin-2-yl)-propionamide.

The compounds of formula I and their pharmaceutically acceptable salts can be prepared by a) reacting a compound of formula

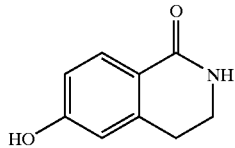

II with a compound of formula

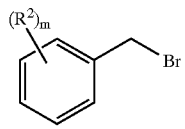

III wherein R² is defined as hereinabove, to obtain a compound of formula

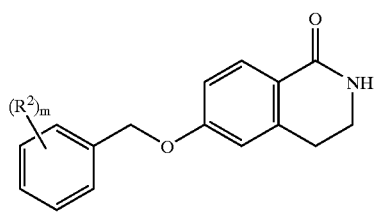

I-A₁ and b) reacting this compound with a compound of formula

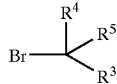

IV wherein R³, R⁴ and R⁵ are defined as hereinabove, to obtain a compound of formula

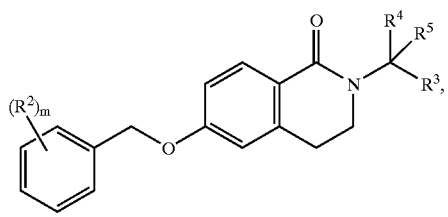

I-A₂ and, if desired, converting a functional group of R³ in a compound of formula I-A₂ into another functional group, and, if desired, converting a compound of formula I into a pharmaceutically acceptable salt.

Alternatively, compounds of formula I may be prepared by a) reducing a compound of formula

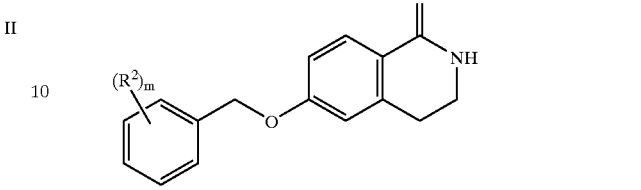

I-A₁ wherein R² is defined as hereinabove, to obtain a compound of formula

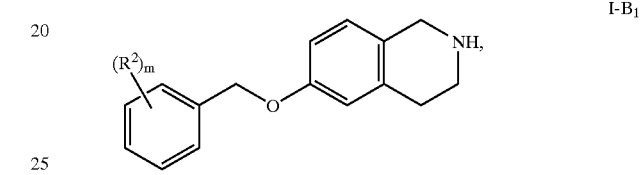

I-B₁ and b) reacting this compound with a compound of formula

IV wherein R³, R⁴ and R⁵ are defined as hereinabove, to obtain a compound of formula

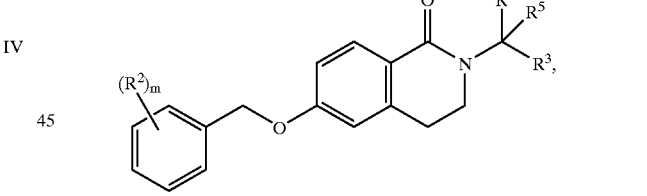

I-B₂

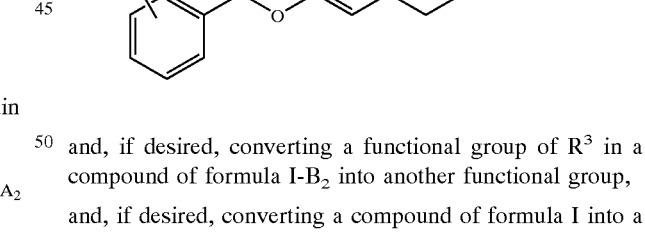

and, if desired, converting a functional group of R³ in a compound of formula I-B₂ into another functional group, and, if desired, converting a compound of formula I into a pharmaceutically acceptable salt.

Compounds of formula I and their pharmaceutically acceptable salts may also be manufactured by a) reacting a compound of formula

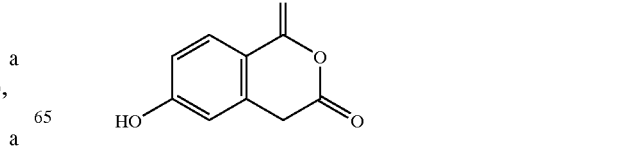

V with a compound of formula

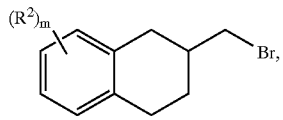

III wherein R² is defined as hereinabove, to obtain a compound of formula

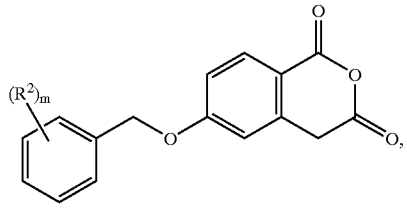

VI and b) reacting this compound with a compound of formula

 H₂N—R    Vii, wherein R¹ is defined as hereinabove, to obtain a compound of formula

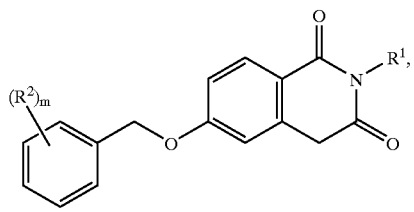

I-C and, if desired, converting a functional group of R¹ in a compound of formula I-C into another functional group, and, if desired, converting a compound of formula I into a pharmaceutically acceptable salt.

Compounds of general formula I and their pharmaceutically acceptable salts can also be manufactured by reacting a compound of formula

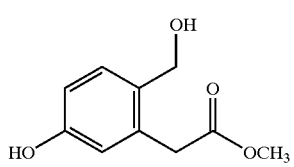

VIII with a compound of formula

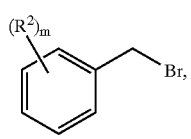

III wherein R² is defined as hereinabove, to obtain a compound of formula

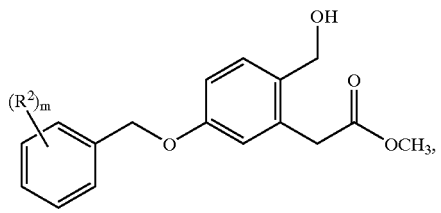

IX and reacting this compound after bromination with a compound of formula

 H₂N—R¹    VII, wherein R¹ is defined as hereinabove, to obtain a compound of formula

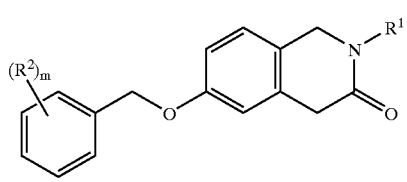

I-D and, if desired, converting a functional group of R¹ in a compound of formula I-D into another functional group, and, if desired, converting a compound of formula I into a pharmaceutically acceptable salt.

Alternatively, compounds of general formula I and their pharmaceutically acceptable salts can be manufactured by oxidation of a compound of formula

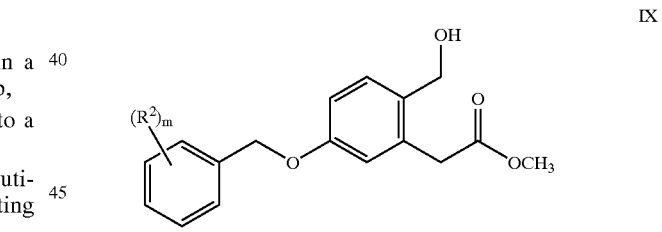

IX to the corresponding aldehyde of formula

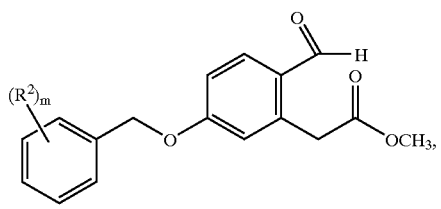

IXa and reacting this compound in the presence of an reducing agent with a compound of formula

 H₂N—R¹    VII, wherein R¹ is defined as hereinabove, to obtain a compound of formula

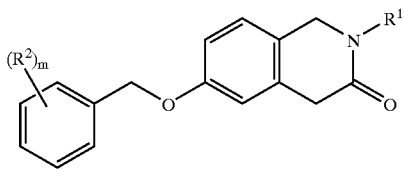

I-D and, if desired, converting a functional group of $R^1$ in a compound of formula I-D into another functional group, and, if desired, converting a compound of formula I into a pharmaceutically acceptable salt.

Compounds of general formula I can also be manufactured stereoselectively by reaction of a compound of formula

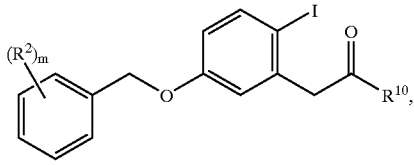

X wherein $R^2$ is defined as hereinabove and $R^{10}$ is hydrogen or hydroxy, with an optically active amino derivative of formula

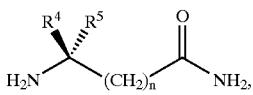

XI wherein $R^4$ and $R^5$ are as defined hereinabove, and reduction to obtain a compound of formula

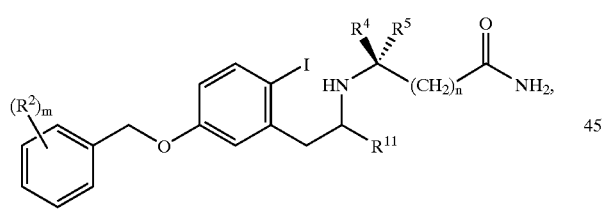

XII wherein $R^{11}$ is hydrogen or oxo, which is reacted with carbon monoxide under pressure in the presence of a palladium (II) salt to obtain a compound of formula

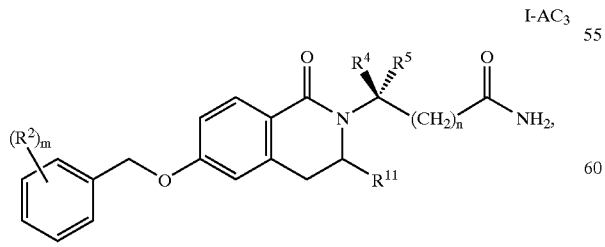

I-AC$_3$ wherein $R^{11}$ is hydrogen or oxo.

In accordance with the present invention, compounds of general formula I-A can be manufactured by refluxing in hydrobromic acid 48% a derivative of formula X to afford compounds of type II. The 6-benzyloxy-3,4-dihydro-2H-isoquinolin-1-one derivative of formula I-A$_1$, wherein $R^1$ is hydrogen, is obtained by coupling with the appropriate benzylic bromide III in the presence of a base like potassium carbonate. The reaction is preferably carried out a temperature of 90° C. in a solvent like N,N'-dimethylformamide. Treatment with sodium hydride and an electrophile of formula IV in a solvent like N,N'-dimethyl-formamide affords compounds of formula I-A$_2$ (scheme 1).

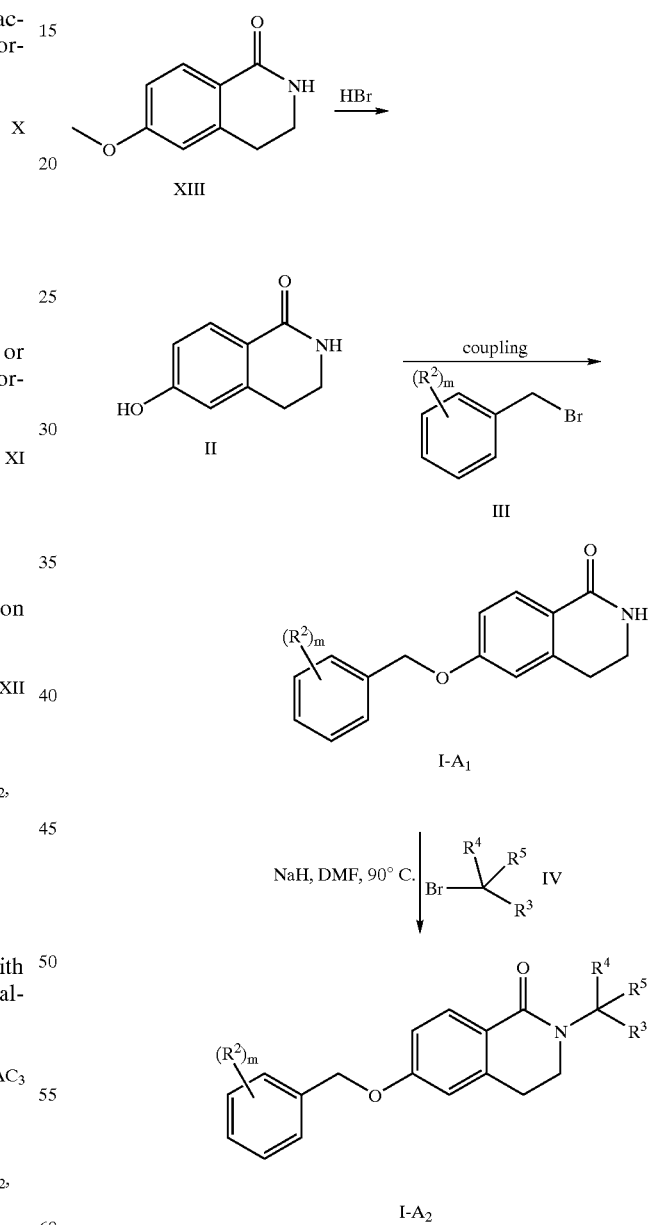

Scheme 1

Compounds of general formula XIII, wherein X signifies —CH═, can be prepared by heating 5-methoxy-1-indanone XIV with sodium azide in benzene in the presence of sulfuric acid (scheme 2).

Scheme 2

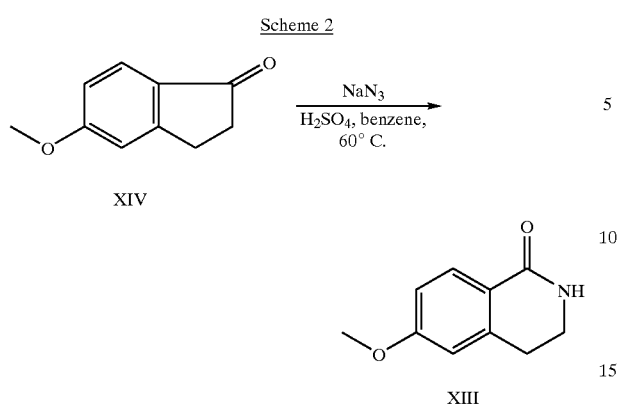

Compounds of formula I-A$_5$, wherein R$^3$ is —(CH$_2$)$_n$—COOR$^8$, wherein R$^8$ signifies hydrogen, can be prepared by reacting a derivative of general formula I-A$_4$ with a base such as lithium hydroxide in a mixture of solvents such as tetrahydrofuran and water (scheme 3).

Scheme 3

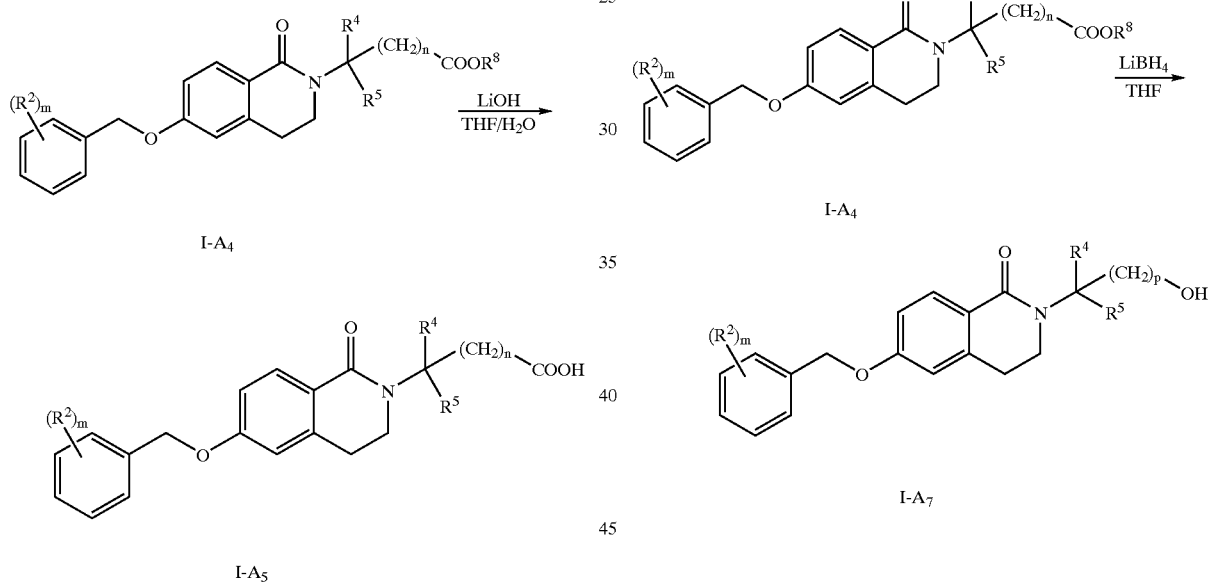

Compounds of formula I-A$_6$, wherein R$^3$ is —(CH$_2$)$_n$—CONR$^6$R$^7$, can be prepared by reacting the corresponding acid with an amine of general formula VIII. The acid is activated with 1,1'-carbonyl-diimidazole (CDI) in N,N'-dimethylformamide (DMF) and ammonium acetate or the amine is added (scheme 4).

Scheme 4

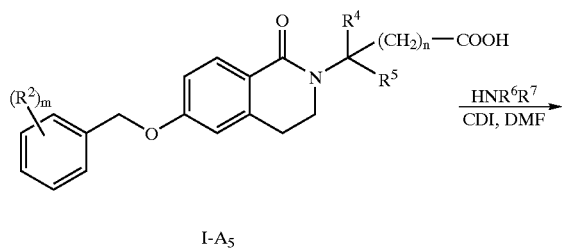

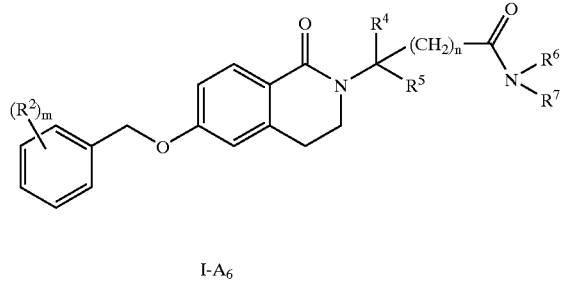

Some compounds of formula I-A$_7$, wherein R$^3$ is —(CH$_2$)$_p$—OH, can be prepared from the reduction of the corresponding ester of formula I-A$_4$ with lithium borohydride in tetrahydrofuran (scheme 5).

Scheme 5

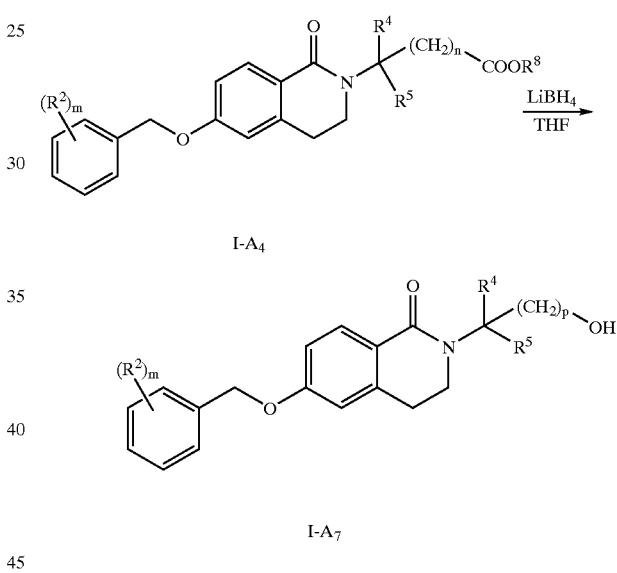

Compounds of formula I-A$_8$, wherein R$^3$ is —(CH$_2$)$_p$—OR$^8$, wherein R$^8$ signifies C$_1$–C$_6$-alkyl, can be prepared from alkylation of the corresponding alcohol with sodium hydride in the presence of the alkylating agent, e.g. R$^8$Br (scheme 6).

Scheme 6

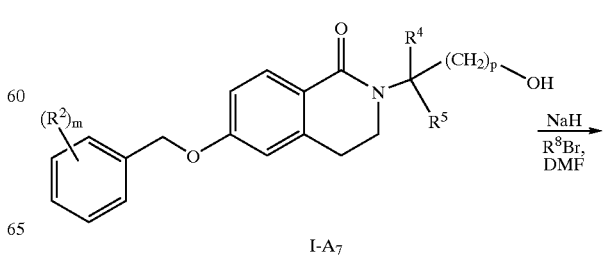

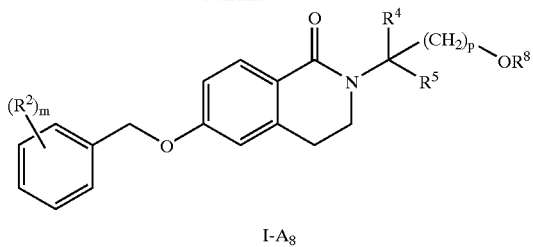

I-A₈

In accordance with the present invention, compounds of general formula I-A₂ can be manufactured by esterification of the 3-hydroxyphenyl-acetic acid XV with methanol and sulfuric acid and ether formation with the appropriate benzyl bromide in the presence of a base like potassium carbonate. Regioselective iodination with iodine in acetic acid and reagents like silver acetate and reduction of the ester to the aldehyde with for example diisobutylaluminum hydride (DIBAH) leads to compounds of formula Xa. Reductive amination with the corresponding α-aminoamide in a solvent like methanol and in the presence of sodium cyanoborohydride gives the necessary intermediate XIIa for the carbonylation. The carbonylation-cyclization reaction is preferably carried out at about 106° C. in a solvent like ethylacetate in the presence of a base like triethylamine or sodium acetate and a Pd catalyst like bis (triphenylphosphine) palladium II chloride to afford compounds of formula I-A₂ (scheme 7).

Scheme 7

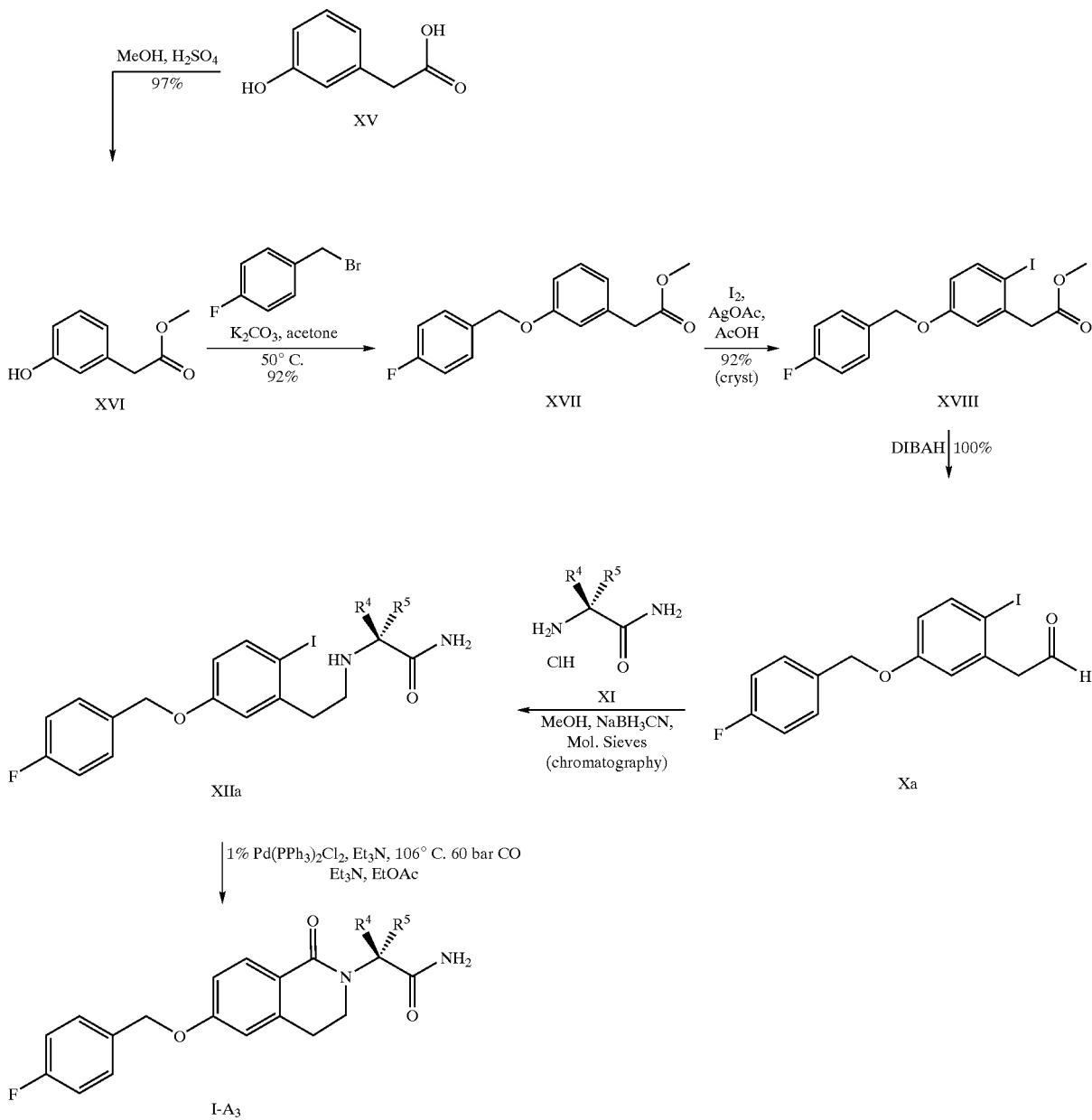

Some compounds of formula I-A$_7$, wherein R$^4$ and R$^5$ are methyl, can be prepared from alkylation of the propionic ester I-A$_8$ with bases like lithium bis(trimethylsilyl) amide in the presence of iodomethane to give the isobutyric ester I-A$_{10}$ that is saponified with lithium hydroxide to give the acid I-A$_{11}$. Coupling with the corresponding amine in the presence of activating agents like PyBOP and HOBt gives the β,β-dimethylated amide (scheme 8).

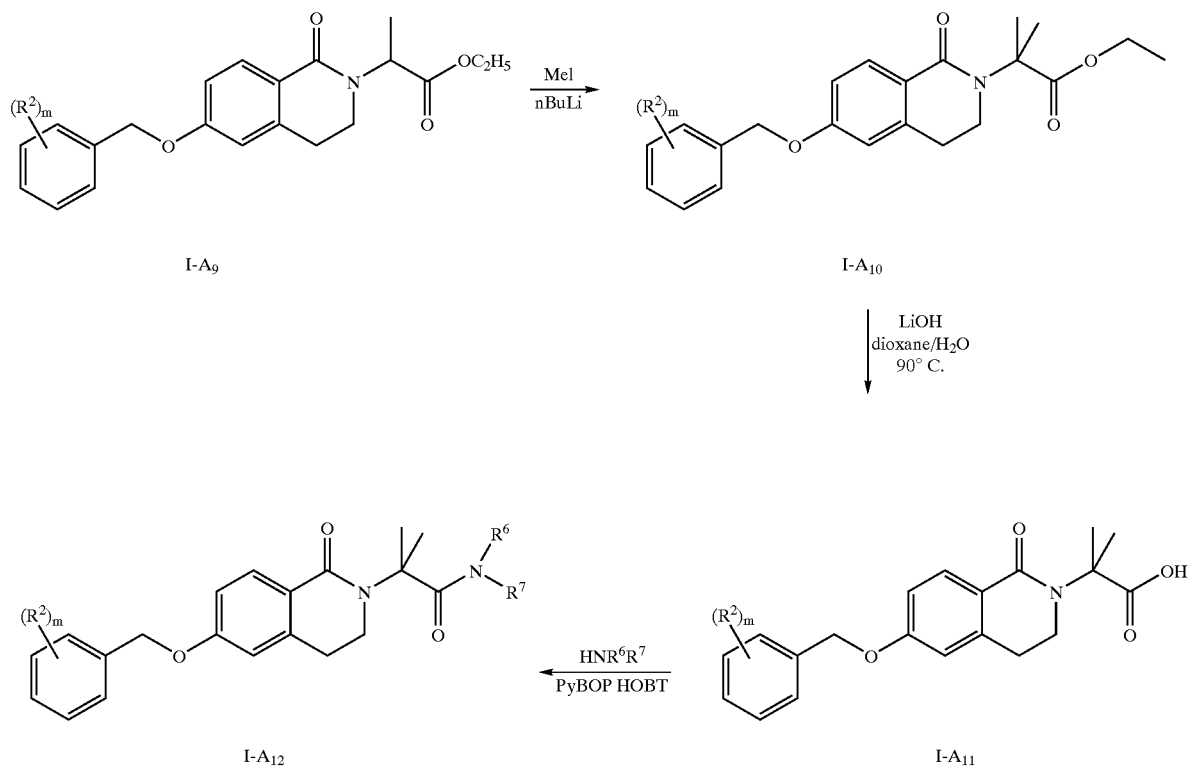

Scheme 8

Other chiral or not chiral derivatives could be prepared from the chiral or not chiral phenol A$_{14}$ that could be obtained by hydrogenation of the enantiomerically pure or from the racemic material respectively as shown in scheme 9. Alkylation of the phenol intermediates using a base like potassium bicarbonate or Mitsunobu conditions open the possibility to obtain a big number of compounds by using different alkylating agents.

Scheme 9

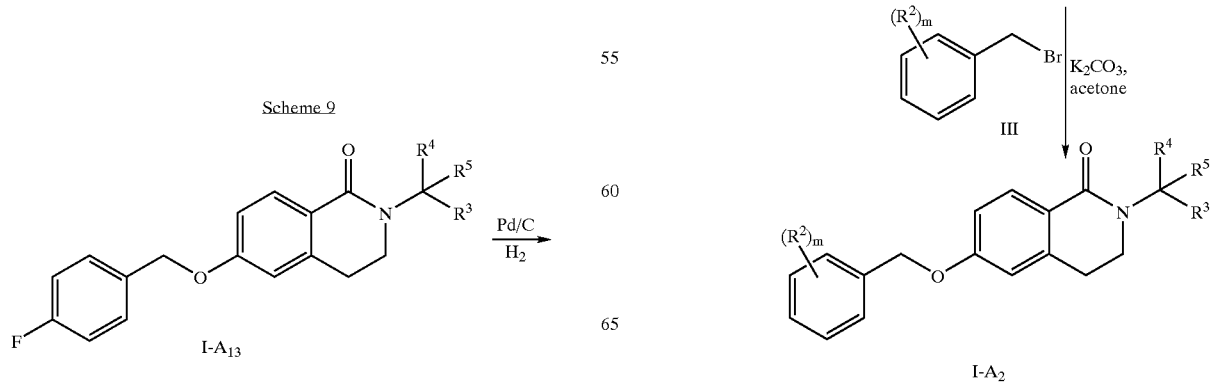

Compounds of general formula I-B$_1$, wherein R$^1$ is hydrogen can be manufactured by treating a derivative of formula I-A$_1$ with lithium aluminum hydride to afford compounds of type I-B. The 6-benzyloxy-3,4-dihydro-1H-isoquinoline derivative of formula I-B$_1$ wherein R$^1$ is hydrogen, is treated with sodium hydride and an electrophile of formula IV in a solvent like dimethylformamide to afford compounds of formula I-B$_2$ (scheme 10):

Scheme 10

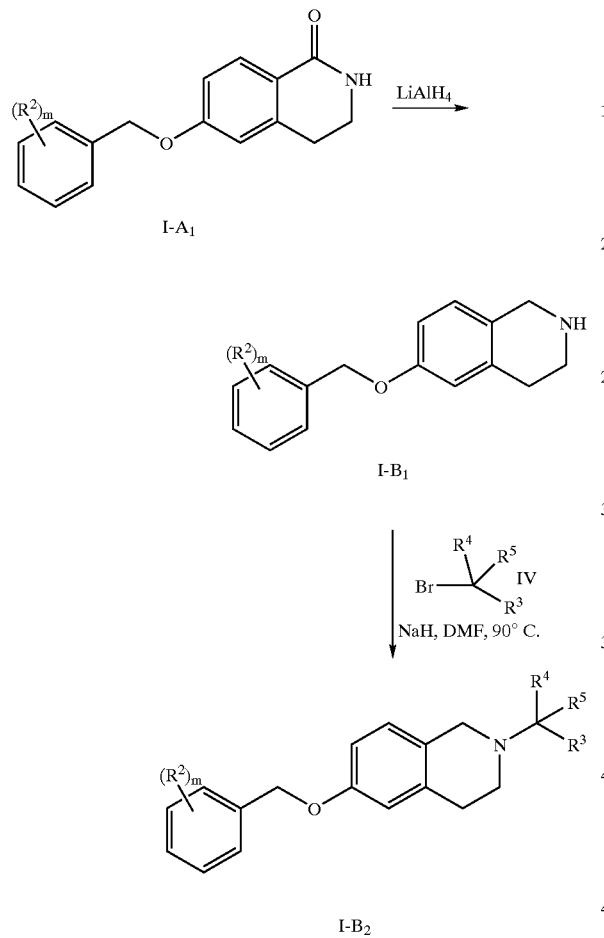

Compounds of formula I-B, wherein R$^3$ is —(CH$_2$)$_n$—COOH, —(CH$_2$)$_n$—CONR$^6$R$^7$, —(CH$_2$)$_p$—OH or —(CH$_2$)$_p$—OR$^8$, can be prepared with analogous methods as described in schemes 3 to 6. For example, compounds of formula I-B$_4$, wherein R$^3$ is —(CH$_2$)$_p$-OH, can be prepared from the reduction of the corresponding ester of formula I-B$_3$ with lithium borohydride in tetrahydrofurane (scheme 11).

Scheme 11

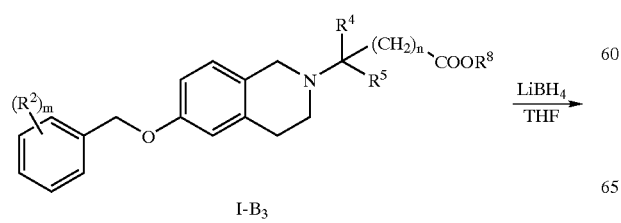

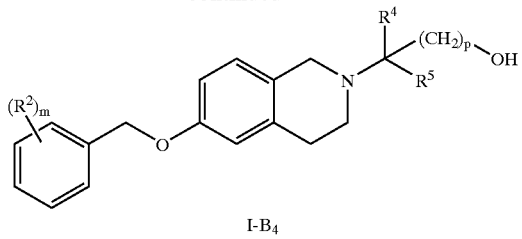

Compounds of formula I-C can be prepared by starting from a 1,3-isochromanone derivative of formula V. Scheme 12 describes the synthesis of a compound of formula V from an acid of formula IXX.

Scheme 12

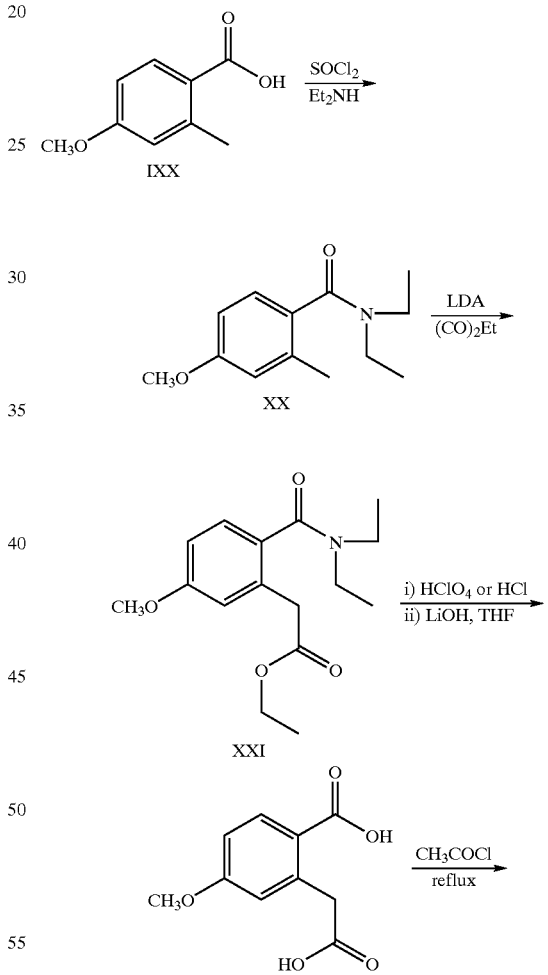

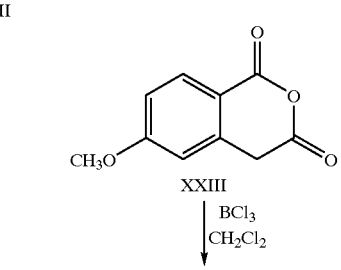

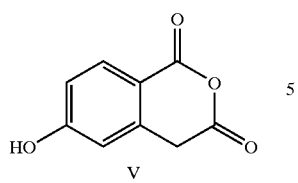

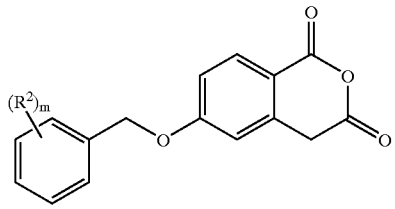

The 6-benzyloxy-1,3-isochromandione derivative of formula VI is then prepared by coupling with the appropriate benzylic bromide III in the presence of a base like potassium carbonate. Compounds of formula I-C can be obtained by reacting a compound of formula VI with an amine of formula VII (or its hydrochloride salt) under basic conditions or heating in an appropriate solvent (scheme 13).

Scheme 13

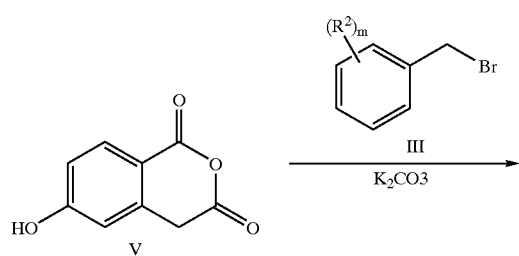

Compounds of formula I-C$_1$, can be prepared via saponification of the 5-(4-fluoro-benzyloxy)-2-iodo-phenyl]-acetic acid methyl ester XVIII (see scheme 7) to the corresponding acid. The acid is activated with 1,1'-carbonyl-diimidazole (CDI) in N,N'-dimethylformamide (DMF) and the corresponding α-aminoamide is added. When the hydrochloride salt of the α-aminoamide is used one equivalent of a base like pyridine needs to be added to the reaction mixture. The compound XXVII obtained, is the adequate for a carbonylation-cyclization reaction that is preferably carried out at a temperature of 106° C. in a solvent like ethylacetate in the presence of a base like triethylamine or sodium acetate and a Pd catalyst like bis(triphenylphosphine) palladium II chloride (scheme 14).

Scheme 14

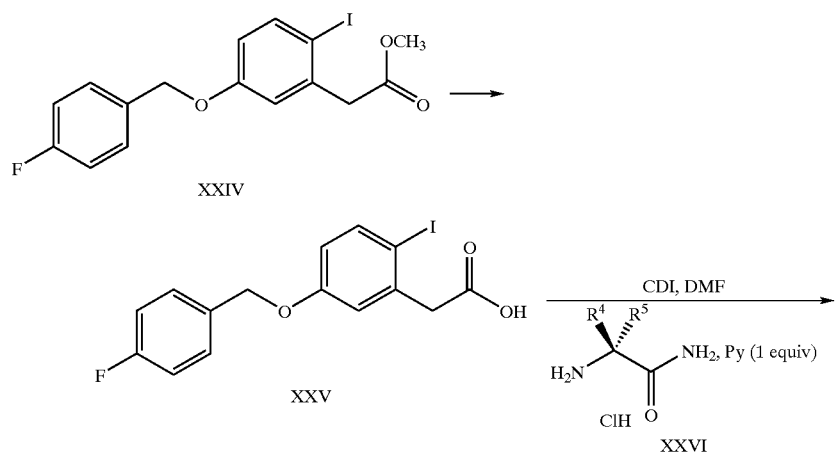

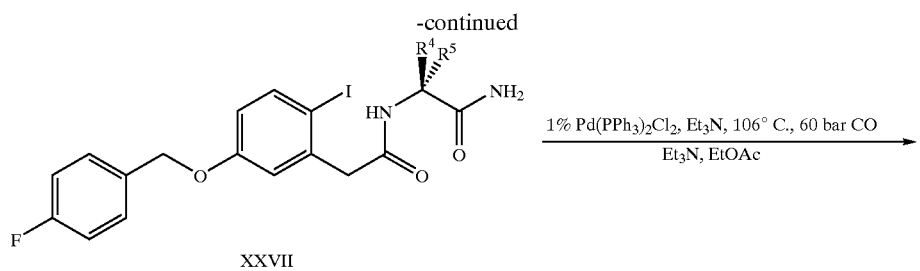
XXVII
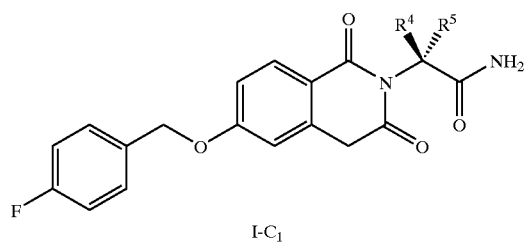
I-C₁
Compounds of formula I-D can be prepared by coupling a compound of formula VIII with a benzylic bromide III in the presence of a base like potassium carbonate to obtain a compound of formula IX. After bromination this compound is reacted with an appropriate amine of formula VII and cyclization to a compound of formula I-D occurs (scheme 15).
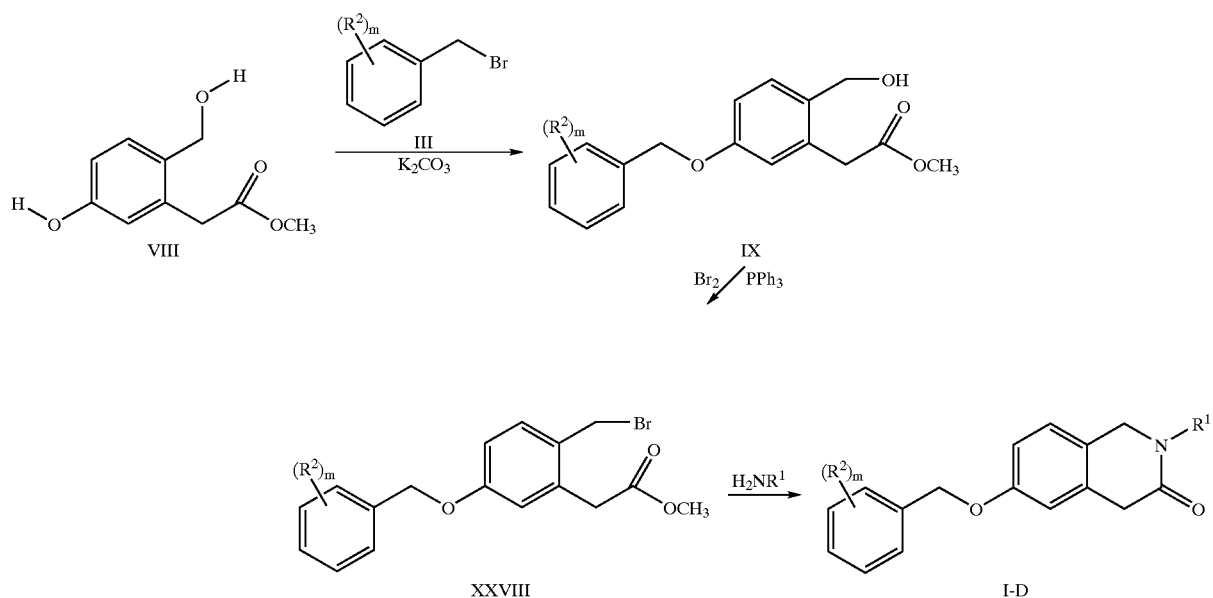

The compound of formula VII can be prepared following scheme 16.

2-oximinoindan-1-one XXXIX was obtained by a modification of a reported procedure (Chakravarti and

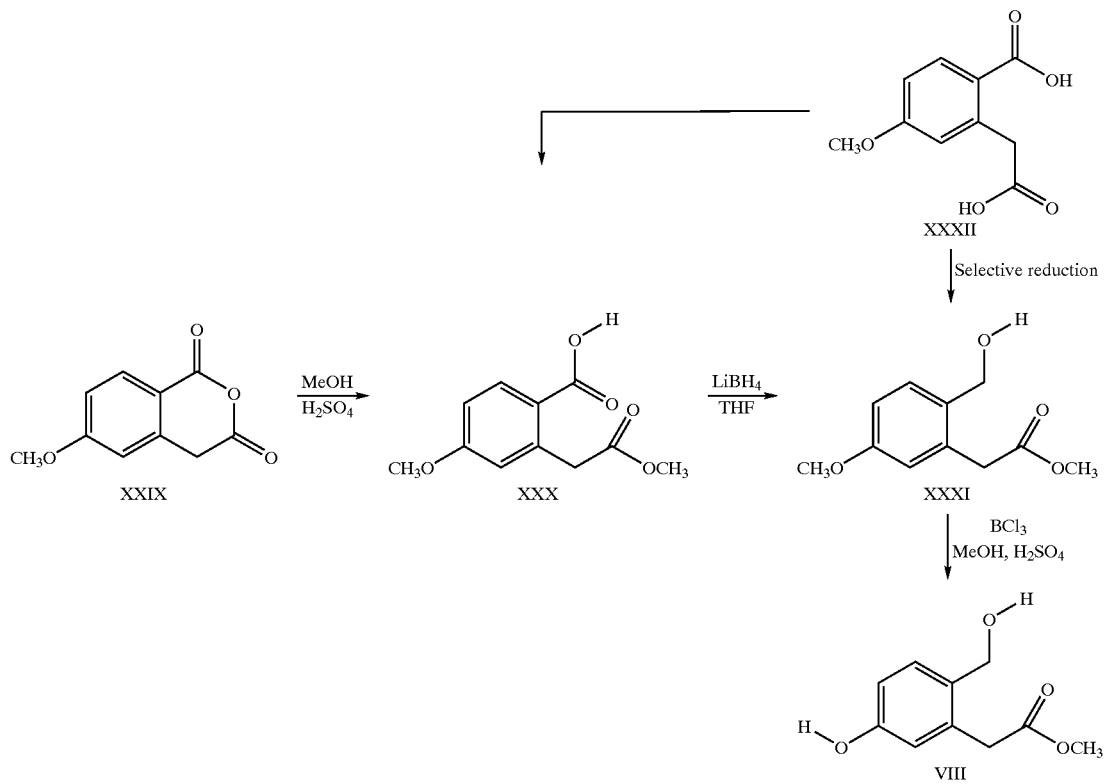

Scheme 16

Alternatively, compounds of formula I-D may be prepared following scheme 17.

Swaminathan, J. Ind. Chem. Soc., 1934, 11, 101) using isoamyl nitrite in methyl cellosolve and HCl. The diacid was

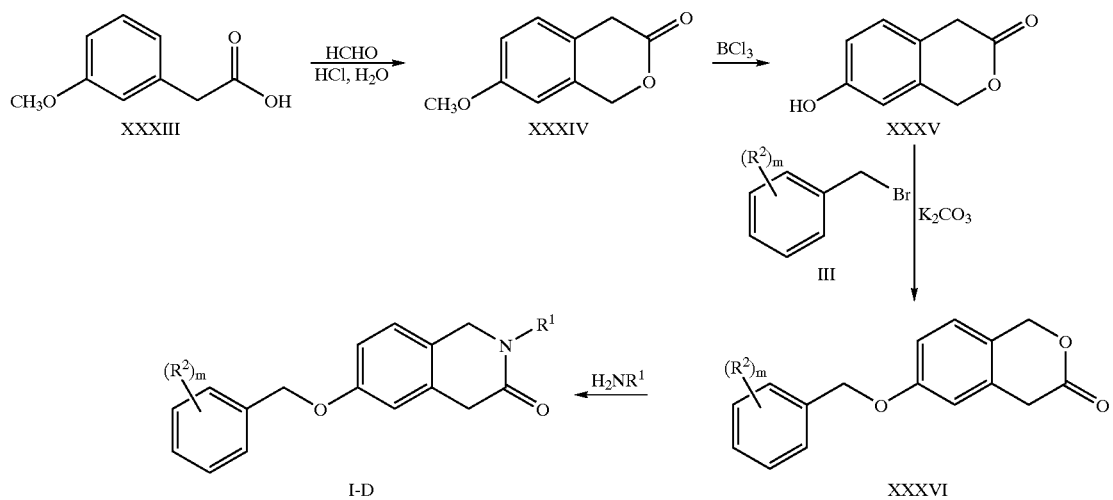

Scheme 17

Yet another method of preparing compounds of formula 1-D is shown in scheme 18. The 5-hydroxy-1-indanone was alkylated with the appropriate benzyl bromide in the presence of a base like potassium carbonate. The 5-benzyloxyobtained by refluxing the isonitroso compound with toluene-p-sulfonyl chloride and sodium hydroxide, addition of more sodium hydroxide and prolongated time of reactions gave directly the hydrolysis of the intermediate nitrile formed in the course of the reaction. Refluxing of the diacid with acetyl chloride gives the benzylic homophthalic anhydride VI. A suspension in absolute methanol was refluxed for 2 hours to get the regioselective formation of the desired mono-methyl ester XXXXI. Reduction of the acid to the alcohol with borane-dimethylsulfide complex in a solvent like THF and the alcohol oxidation with $MnO_2$ in $CHCl_3$ or preferably using Swern conditions gives the aldehyde XXXXII that is necessary for the reductive amination with the corresponding α-aminoamide in a solvent like methanol and in the presence of sodium cyanoborohydride in order to get the precursor XXXXIII for the final cyclization step. The cylization can be obtained by heating XXXXIII in toluene and preferably with an Deam-stark in order to remove the methanol formed in the reaction (scheme 18).

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

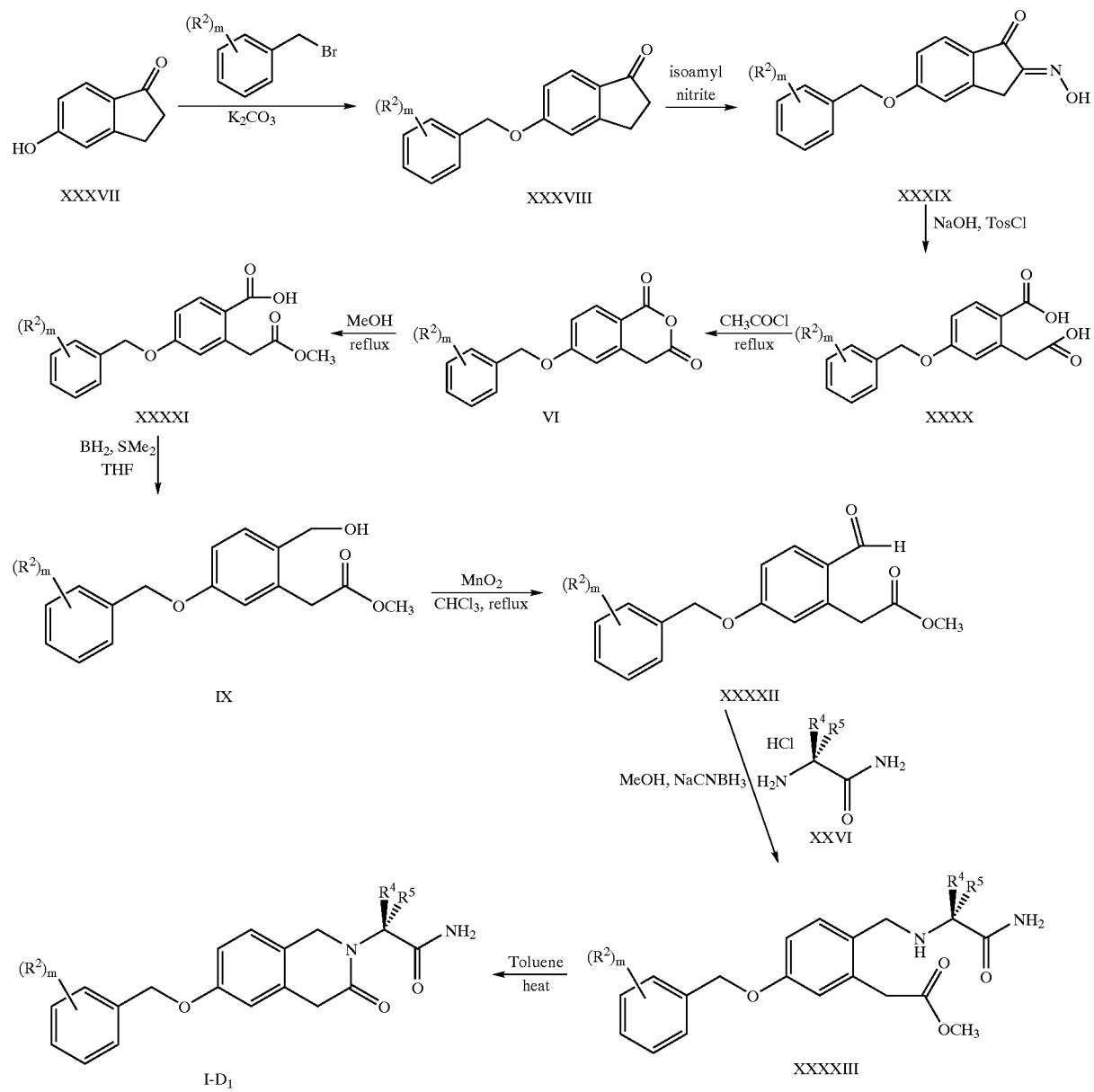

Scheme 18

The compounds of the invention and their pharmaceutically acceptable salts are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (G. M. Sullivan, International patent application No. WO 01/34172 A2), peripheral neuropathy caused by cancer chemotherapy (G. Bobotas, International Patent Application No. WO 97/33572 A1), or the treatment of multiple sclerosis (R. Y. Harris, International patent application No. WO 96/40095 A1) and other neuroinflammatory diseases.

The compounds of formula I and their pharmaceutically acceptable salts are especially useful for the treatment and prevention of Alzheimer's disease and senile dementia.

The pharmacological activity of the compounds of the invention was determined using the following method:

The cDNA's encoding human MAO-A and MAO-B were transiently transfected into EBNA cells using the procedure described by E.-J. Schlaeger and K. Christensen (Transient Gene Expression in Mammalian Cells Grown in Serum-free Suspension Culture; Cytotechnology, 15: 1–13, 1998). After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by M. Zhou and N. Panchuk-Voloshina (A One-Step Fluorometric Method for the Continuous Measurement of Monoamine Oxidase Activity, Analytical Biochemistry, 253: 169174, 1997). Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 μM N-acetyl-3,7,-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B.

$IC_{50}$ values, that is, the concentration of a test compound according to the invention required to inhibit the MAO-B enzyme activity by 50%, were determined from inhibition curves obtained using nine inhibitor concentrations in duplicate, by fitting data to a four parameter logistic equation using a computer program.

The compounds of the present invention are specific MAO-B inhibitors. The $IC_{50}$ values of compounds of formula I as measured in the assay described above are in the range of 10 μM or less, typically of 1 μM or less, ideally 0.03 μM or less, and more preferably 0.1 μM or less.

In the table below are described some specific $IC_{50}$ values of preferred compounds.

| Compound | $IC_{50}$ MAO-B (μM) | $IC_{50}$ MAO-A (μM) |
|---|---|---|
| 6-(3-fluoro-benzyloxy)-3,4-dihydro-2H-isoquinolin-1-one (example 1) | 0.104 | 5.24 |
| 2-[6-(3-fluoro-benzyloxy)-1-oxo-3,4-dihydro-1H-isoquinolin-2-yl]-acetamide (example 6) | 0.008 | 0.33 |
| 2-[6-(3-fluoro-benzyloxy)-1-oxo-3,4-dihydro-1H-isoquinolin-2-yl]-propionamide (example 7) | 0.012 | >10 |
| 6-(3-fluoro-benzyloxy)-2-(2-hydroxy-1-methyl-ethyl)-3,4-dihydro-2H-isoquinolin-1-one (example 8) | 0.074 | >10 |
| [6-(3-fluoro-benzyloxy)-1-oxo-3,4-dihydro-1H-isoquinolin-2-yl]-acetonitrile (example 12) | 0.154 | — |
| 6-(3-fluoro-benzyloxy)-2-(2-methoxy-1-methyl-ethyl)-3,4-dihydro-2H-isoquinolin-1-one (example 14) | 0.063 | 4.22 |
| 3-[6-(3-fluoro-benzyloxy)-1-oxo-3,4-dihydro-1H-isoquinolin-2-yl]-propionamide (example 19) | 0.392 | — |
| 2-(R)-[6-(4-fluoro-benzyloxy)-1-oxo-3,4-dihydro-1H-isoquinolin-2-yl]-propionamide (example 20) | 0.012 | >10 |
| 2-(S)-[6-(4-fluoro-benzyloxy)-1-oxo-3,4-dihydro-1H-isoquinolin-2-yl]-propionamide (example 21) | 0.018 | >10 |
| 2-(S)-[6-(4-fluoro-benzyloxy)-1-oxo-3,4-dihydro-1H-isoquinolin-2-yl]-3-hydroxy-propionamide (example 22) | 0.020 | >10 |
| 2-[6-(4-fluoro-benzyloxy)-1-oxo-3,4-dihydro-1H-isoquinolin-2-yl]-isobutyramide (example 30) | 1.13 | — |
| 2-[6-(3-fluoro-benzyloxy)-3,4-dihydro-1H-isoquinolin-2-yl]-propionamide (example 32) | 0.013 | >10 |
| 2-[6-(4-fluoro-benzyloxy)-3,4-dihydro-1H-isoquinolin-2-yl]-propionamide (example 37) | 0.012 | 3.43 |
| 2-(2-ethoxy-ethyl)-6-(3-fluoro-benzyloxy)-1,2,3,4-tetrahydro-isoquinoline (example 39) | 0.097 | >10 |
| 6-(4-fluoro-benzyloxy)-2-(tetrahydro-furan-2-ylmethyl)-1,2,3,4-tetrahydro-isoquinoline (example 42) | 0.075 | 5.92 |
| 2-(R)-[6-(4-fluoro-benzyloxy)-1,3-dioxo-3,4-dihydro-1H-isoquinolin-2-yl]-propionamide (example 45) | 0.058 | >10 |
| 2-(S)-[6-(4-fluoro-benzyloxy)-3-oxo-3,4-dihydro-1H-isoquinolin-2-yl]-propionamide (example 47) | 0.015 | >10 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof.

EXAMPLE 1

6-(3-Fluoro-benzyloxy)-3,4-dihydro-2H-isoquinolin-1-one a) 6-Methoxy-3,4-dihydro-2H-isoquinolin-1-one Sulfuric acid (82.6 mL) was carefully added, at 0° C., to 5-methoxy-1-indanone (25 g, 154 mmol) in benzene (400 mL) followed by sodium azide (18 g, 277.4 mmol). The resulting mixture was heated at 60° C. for 24 h. After cooling at room temperature, the benzene was evaporated and the resulting mixture was diluted with water and extracted with dichloromethane. After drying of the organic layer with $MgSO_4$, filtration and evaporation the product was obtained as a white solid after purification by chromatography ($SiO_2$, ethyl acetate/n-hexane 1:1 to 4:1 v:v gradient) (13.2 g, 49%). MS: m/e=177.2 (M+)

b) 6-Hydroxy-3,4-dihydro-2H-isoquinolin-1-one

The 6-methoxy-3,4-dihydro-2H-isoquinolin-1-one (10 g, 56.4 mmol) was dissolved in hydrobromic acid 48% in water (216 mL) and refluxed for 72 h at 95° C. After cooling to 0° C. a saturated solution of ammonium hydroxide was added and the mixture extracted with ethyl acetate. After drying of the organic layer with $MgSO_4$, filtration and evaporation, the residue was purified by chromatography ($SiO_2$, $CH_2Cl_2$/MeOH 1:0 to 9:1 v:v gradient) to give the title alcohol as a brown solid (6 g, 65%). MS: m/e=162.2 (M−H+).

c) 6-(3-Fluoro-benzyloxy)-3,4-dihydro-2H-isoquinolin-1-one

A mixture of 6-hydroxy-3,4-dihydro-2H-isoquinolin-1-one (0.400 g, 2.44 mmol), 3-fluorobenzyl bromide (0.509 g, 2.69 mmol), potassium carbonate (0.372 g, 2.69 mmol) and N,N-dimethylformamide (5 ml) was heated to 90° C. for 8 h. Water was added and the resulting precipitate was washed with diethylether and then dried under high vacuum to afford the title compound (0.580 g, 87%). MS: m/e=272.3 (M+H+).

EXAMPLE 2

2-[6-(3-Fluoro-benzyloxy)-1-oxo-3,4-dihydro-1H-isoquinolin-2-yl]-propionic acid ethyl ester A mixture of 6-(3-fluoro-benzyloxy)-3,4-dihydro-2H-isoquinolin-1-one (0.100 g, 0.369 mmol) and sodium hydride (55%, 22 mg, 0.51 mmol) in N,N'-dimethylformamide was heated at 70° C. for 1 h. Then ethyl-2-bromopropionate (0.072 mL, 0.55 mmol) was added and the resulting mixture was heated at 80° C. overnight. After cooling to room temperature, water was added and the reaction was extracted with dichloromethane. After drying of the organic layer with $MgSO_4$, filtration and evaporation, the residue was purified by chromatography ($SiO_2$, hexane/ethyl acetate 1:0 to 3:2 v:v gradient) to give the title compound as a white solid (0.095 g, 69%). MS: m/e=372.3 (M+H+).

EXAMPLE 3

2-[6-(3-Fluoro-benzyloxy)-1-oxo-3,4-dihydro-1H-isoquinolin-2-yl 1-propionic acid A mixture of the 2-[6-(3-fluoro-benzyloxy)-1-oxo-3,4-dihydro-1H-isoquinolin-2-yl]-propionic acid ethyl ester (0.087 g, 0.234 mmol) (example 2) and lithium hydroxide (0.0062 g, 0.258 mmol) in water and tetrahydrofuran (1:1 v:v, 9 mL) was stirred at room temperature for 2 h. The THF was evaporated and the mixture acidified to pH 3–4 with 0.1N HCl. After extraction with ethyl acetate, drying of the organic layer with $MgSO_4$, filtration and evaporation a white solid was obtained (0.080 g, 99%). MS: m/e=342.1 (M−H+).

EXAMPLE 4

[6-(3-Fluoro-benzyloxy)-1-oxo-3,4-dihydro-1H-isoquinolin-2-yl]-acetic acid ethyl ester As described for example 2, the 6-(3-fluoro-benzyloxy)-3,4-dihydro-2H-isoquinolin-1-one (0.300 g, 1.1 mmol) was converted to the title compound (0.270 g, 68%) using ethylbromoacetate instead ethyl-2-bromopropionate (0.183 mL, 1.66 mmol). MS: m/e=358.3 (M+H+).

EXAMPLE 5

[6-(3-Fluoro-benzyloxy)-1-oxo-3,4-dihydro-1H-isoquinolin-2-yl]-acetic acid

As described for example 3, the 6-(3-fluoro-benzyloxy)-1-oxo-3,4-dihydro-1H-isoquinolin-2-yl]-acetic acid ethyl ester (0.270 g, 0.775 mmol) (example 4) was converted to the title compound which was obtained as a white solid (0.247 mg, 99%). MS: m/e=328.1 (M−Ht).

EXAMPLE 6

2-[6-(3-Fluoro-benzyloxy)-1-oxo-3,4-dihydro-1H-isoquinolin-2-yl]-acetamide

A mixture of [6-(3-fluoro-benzyloxy)-1-oxo-3,4-dihydro-1H-isoquinolin-2-yl]-acetic acid (0.245 mg, 0.744 mmol) and 1,1'-carbonyl-diimidazole (0.229 mg, 1.41 mmol) in N,N'-dimethylformamide (6 mL) was stirred at room temperature for 0.5 h. Ammonium acetate (0.917 g, 11 mol) was added and the mixture was stirred 2 h. Water was added and the mixture was extracted with ethyl acetate. Drying and evaporation of the solvent left a solid which was recrystallised with ethyl acetate and ether. MS: m/e=329.3 (M+H$^+$).

EXAMPLE 7

2-[6-(3-Fluoro-benzyloxy)-1-oxo-3,4-dihydro-1H-isoquinolin-2-yl]-propionamide

As described in example 6, the 2-[6-(3-fluoro-benzyloxy)-1-oxo-3,4-dihydro-1H-isoquinolin-2-yl]-propionic acid (0.080 g, 0.232 mmol) (example 3) was converted to the title compound which was obtained as a white solid (0.069 mg, 87%). MS: m/e=343.3 (M+H$^+$).

EXAMPLE 8

6-(3-Fluoro-benzyloxy)-2-(2-hydroxy-1-methyl-ethyl)-3,4-dihydro-2H-isoquinolin-1-one The 2-[6-(3-fluoro-benzyloxy)-1-oxo-3,4-dihydro-1H-isoquinolin-2-yl]-propionic acid (see example 3) (0.029 g, 0.058 mmol) was diluted in tetrahydrofuran (0.5 mL) and borane-methyl sulfide complex was added (0.017 mL, 0.175 mmol) at −20° C. The mixture was stirred 2 h from −20° C. to room temperature. Methanol was added and the solvents evaporated under vacuum. The resulting solid formed was purified by chromatography (SiO$_2$, CH$_2$Cl$_2$/MeOH 9:1 v:v) to give the title compound as a white solid (0.018 g, 94%). MS: m/e=330.4 (M+H$^+$).

EXAMPLE 9

6-(3-Fluoro-benzyloxy)-2-(2-hydroxy-ethyl)-3,4-dihydro-2H-isoquinolin-1-one

As described for example 8, the 6-(3-fluoro-benzyloxy)-1-oxo-3,4-dihydro-1H-isoquinolin-2-yl]-acetic acid (0.030 g, 0.091 mmol) (example 5) was converted to the title compound (0.018 g, 62%). MS: m/c=316.3 (M+H$^+$).

EXAMPLE 10

2-[6-(4-Fluoro-benzyloxy)-1-oxo-3,4-dihydro-1H-isoquinolin-2-yl]-propionamide a) 6-(4-Fluoro-benzyloxy)-3,4-dihydro-2H-isoquinolin-1-one As described for example 1c, 6-(4-fluoro-benzyloxy)-3,4-dihydro-2H-isoquinolin-1-one was prepared from a mixture of 6-hydroxy-3,4-dihydro-2H-isoquinolin-1-one (0.200 g, 1.22 mmol), 4-fluorobenzyl bromide (0.151 mL, 1.22 mmol), potassium carbonate and N,N-dimethylformamide (0.237 g, 72%). MS: m/e=271.2 (M$^+$).

b) 2-[6-(4-Fluoro-benzyloxy)-1-oxo-3,4-dihydro-1H-isoquinolin-2-yl]-propionic acid ethyl ester As described for example 2,6-(4-fluoro-benzyloxy)-3,4-dihydro-2H-isoquinolin-1-one (0.200 g, 0.737 mmol) was converted to the title compound (0.240 g, 88%). MS: m/e 372.3 (M+H$^+$).

c) 2-[6-(4-Fluoro-benzyloxy)-1-oxo-3,4-dihydro-1H-isoquinolin-2-yl]-propionic acid As described for example 3, 2-[6-(4-fluoro-benzyloxy)-1-oxo-3,4-dihydro-1H-isoquinolin-2-yl]-propionic acid ethyl ester (0.240 g, 0.65 mmol) was converted to the title compound (0.153 g, 69%). MS: m/e=344.3 (M+H$^+$).

d) 2-[6-(4-Fluoro-benzyloxy)-1-oxo-3,4-dihydro-1H-isoquinolin-2-yl]-propionamide As described for example 6, 2-[6-(4-fluoro-benzyloxy)-1-oxo-3,4-dihydro-1H-isoquinolin-2-yl]-propionic acid (0.100 g, 0.291 mmol) was converted to the title compound (0.088 g, 88%). MS: m/e=343.3 (M+H$^+$).

EXAMPLE 11

2-[6-(3,4-Difluoro-benzyloxy)-1-oxo-3,4-dihydro-1H-isoquinolin-2-yl]-propionamide a) 6-(3,4-Fluoro-benzyloxy)-3,4-dihydro-2H-isoquinolin-1-one As described for example 1c, 6-(3,4-fluoro-benzyloxy)-3,4-dihydro-2H-isoquinolin-1-one was prepared from a mixture of 6-hydroxy-3,4-dihydro-2H-isoquinolin-1-one (0.200 g, 1.2 mmol), 3,4-fluorobenzyl bromide (0.158 mL, 1.22 mmol), potassium carbonate and N,N-dimethylformamide (0.184 g, 51%). MS: m/e=322.3 (M+H$^+$).

b) 2-[6-(3,4-Fluoro-benzyloxy)-1-oxo-3,4-dihydro-1H-isoquinolin-2-yl]-propionic acid ethyl ester As described for example 2,6-(3,4-fluoro-benzyloxy)-3,4-dihydro-2H-isoquinolin-1-one (0.170 g, 0.588 mmol) was converted to the title compound (0.132 g, 58%). MS: m/e =390.3 (M+H$^+$).

c) 2-[6-(3,4-Fluoro-benzyloxy)-1-oxo-3,4-dihydro-1H-isoquinolin-2-yl]-propionic acid As described for example 3, 2-[6-(4-fluoro-benzyloxy)-1-oxo-3,4-dihydro-1H-isoquinolin-2-yl]-propionic acid ethyl ester (0.130 g, 0.334 mmol) was converted to the title compound (0.110 g, 92%). MS: m/e=362.3 (M+H$^+$).

d) 2-[6-(3-Difluoro-benzyloxy)-1-oxo-3,4-dihydro-1H-isoquinolin-2-yl]-propionamide As described for example 6,2-[6-(3,4-fluoro-benzyloxy)-1-oxo-3,4-dihydro-1H-isoquinolin-2-yl]-propionic acid (0.100 g, 0.277 mmol) was converted to the title compound (0.078 g, 78%) MS: m/e=361.2 (M+H$^+$).

EXAMPLE 12

[6-(3-Fluoro-benzyloxy)-1-oxo-3,4-dihydro-1H-isoquinolin-2-yl]-acetonitrile

As described for example 2, the 6-(3-fluoro-benzyloxy)-3,4-dihydro-2H-isoquinolin-1-one (0.200 g, 0.74 mmol) was converted to the title compound (0.090 g, 40%) using 2-bromoacetonitrile (0.06 mL, 0.96 mmol) instead of ethyl-2-bromo-propionate. MS: m/c=311.2 (M+H$^+$).

EXAMPLE 13

2-[1-Oxo-6-(4-trifluoromethyl-benzyloxy)-3,4-dihydro-1H-isoquinolin-2-yl]-propionamide a) 6 (4-Trifluoromethyl-benzyloxy)-3,4-dihydro-2H-isoquinolin-1-one As described for example 1c, 6-(4-trifluoromethyl-benzyloxy)-3,4-dihydro-2H-isoquinolin-1-one was prepared from a mixture of 6-hydroxy-3,4-dihydro-2H-isoquinolin-1-one (0.200 g, 1.22 mmol), 4-fluorobenzyl bromide (0.381 g, 1.59 mmol), potassium carbonate and N,N-dimethylformamide (0.365 g, 93%). MS: m/e=322.3 (M+H$^+$).

b) 2-[1-Oxo-6-(4-trifluoromethyl-benzyloxy)-3,4-dihydro-1H-isoquinolin-2-yl]-propionic acid ethyl ester As described for example 2,6-(4-trifluoromethyl-benzyloxy)-3,4-dihydro-2H-isoquinolin-1-one (0.170 g, 0.558 mmol) was converted to the title compound (0.132 g, 58%). MS: m/e=390.3 (M+H$^+$).

c) 2-[1-Oxo-6-(4-trifluoromethyl-benzyloxy)-3,4-dihydro-1H-isoquinolin-2-yl]-propionic acid As described for example 3,2-[1-oxo-6-(4-trifluoromethyl-benzyloxy)-1-oxo-3,4-dihydro-1H-isoquinolin-2-yl]-propionic acid ethyl ester (0.130 g, 0.33 mmol) was converted to the title compound (0.110 g, 91%). MS: m/e=394.3 (M+H+).

d) 2-[1-Oxo-6-(4-trifluoromethyl-benzyloxy)-3,4-dihydro-1H-isoquinolin-2-yl]-propionamide As described for example 6, 2–16-(4-trifluoromethyl-benzyloxy)-1-oxo-3,4-dihydro-1H-isoquinolin-2-yl]-propionic acid (0.050 g, 0.127 mmol) was converted to the title compound (0.020 g, 40%) MS: m/e=393.2 (M+H+).

EXAMPLE 14

6-(3-Fluoro-benzyloxy)-2-(2-methoxy-1-methyl-ethyl)-3,4-dihydro-2H-isoquinolin-1-one To a mixture of 6-(3-Fluoro-benzyloxy)-2-(2-hydroxy-1-methyl-ethyl)-3,4-dihydro-2H-isoquinolin-1-one (0.020 g, 0.061 mmol) and sodium hydride (55%, 2.2 mg, 0.067 mmol) in N,N'-dimethylformamide (0.2 mL), methyl iodide (0.009 mL, 0.152 mmol) was added. Water was added and the reaction was extracted with ethyl acetate. After drying of the organic layer with MgSO₄, filtration and evaporation, the residue was purified by chromatography (SiO₂, hexane/ethyl acetate 9:1 v:v) to give the title compound as a white solid (0.0095 g, 43%). MS: m/e=344.4 (M+H+).

EXAMPLE 15

2-(R)-[6-(3-Fluoro-benzyloxy)-1-oxo-3,4-dihydro-1H-isoquinolin-2-yl]-propionamide The racemic compound obtained in example 7 was separated by chiral HPLC (Chirlapac AD, 20% EtOH/heptane, 280 nm, Flow 1.0 ml). Peak A: Retention Time 55.33 Min. MS: m/e=343.3 (M+H+). [α]$_D$=+125.48 (c=0.3539 g/100 mL))

EXAMPLE 16

6-(3-Fluoro-benzyloxy)-2-(2-methoxy-ethyl)-3,4-dihydro-2H-isoquinolin-1-one

As described for example 2, the 6-(3-fluoro-benzyloxy)-3,4-dihydro-2H-isoquinolin-1-one (0.100 g, 0,37 mmol) was converted to the title compound (0.052 g, 42%) using (2-bromoethyl)-methylether (0.055 mL, 0.59 mmol) instead of ethyl-2-bromopropionate. MS: m/e=330.3 (M+H+).

EXAMPLE 17

3-[63-Fluoro-benzyloxy)-1-oxo-3,4-dihydro-1H-isoquinolin-2-yl]-propionitrile

As described for example 2, the 6-(3-fluoro-benzyloxy)-3,4-dihydro-2H-isoquinolin-1-one (0.100 g, 0.37 mmol) was converted to the title compound (0.048 g, 40%) using 3-bromopropionitrile (0.079 mL, 0.59 mmol) instead of ethyl-2-bromo-propionate. MS: m/e=325.4 (M+H+).

EXAMPLE 18

2-[6-(4-Fluoro-benzyloxy)-1-oxo-3,4-dihydro-1H-isoquinolin-2-yl]-acetamide

As described for example 6, the 6-(4-fluoro-benzyloxy)-1-oxo-3,4-dihydro-1H-isoquinolin-2-yl]-acetic acid (0.200 g, 0.607 mmol) (example 10c) was converted to the title compound (0.140 g, 70%) MS: m/e=329.4 (M+H+).

EXAMPLE 19

3-[6 (3-Fluoro-benzyloxy)-1-oxo-3,4-dihydro-1H-isoquinolin-2-yl]-propionamide a) 3-[6-(3-Fluoro-benzyloxy)-1-oxo-3,4-dihydro-1H-isoquinolin-2-yl]-propionic acid ethyl ester As described for example 2, the 6-(3-fluoro-benzyloxy)-3,4-dihydro-2H-isoquinolin-1-one (0.100 g, 0.37 mmol) was converted to the title compound 0.045 g, 33%) using ethyl-3-bromo-propionate (0.075 mL, 0.59 mmol) instead of ethyl-2-bromo-propionate. MS: m/e=372.3 (M+H+).

b) 3[6-(3-Fluoro-benzyloxy)-1-oxo-3,4-dihydro-1H-isoquinolin-2-yl]-propionic acid As described for example 3,3-[6-(3-fluoro-benzyloxy)-1-oxo-3,4-dihydro-1H-isoquinolin-2-yl]-propionic acid ethyl ester (0.040 g, 0.108 mmol) was converted to the title compound (0.033 g, 89%). MS: m/e=342.1 (M–H+).

c) 3-[6-(3-Fluoro-benzyloxy)-1-oxo-3,4-dihydro-1H-isoquinolin-2-yl]-propionamide As described for example 6, the 3-[6-(3-fluoro-benzyloxy)-1-oxo-3,4-dihydro-1H-isoquinolin-2-yl}-propionic acid (0.030 g, 0.087 mmol) was converted to the title compound (0.024 g, 80%) MS: n/e=343.3 (M+H+).

EXAMPLE 20

2-(R)-[6-(4-Fluoro-benzyloxy)-1-oxo-3,4-dihydro-1H-isoquinolin-2-yl]-propionamide a) (3-Hydroxy-phenyl)-acetic acid methyl ester 3-hydroxyphenylacetic acid (111 g, 735.84 mmol) was dissolved under argon in 1000 ml methanol and then sulfuric acid (31.5 mL, 588.6 mmol) was added. The brown mixture was heated (70° C.) for 3 hours, at this temperature, and then cooled to room temperature. The mixture was concentrated in a rotary evaporator and then cooled down to 0° C. 250 mL water and 70 g of NaHCO₃ were added with stirring, until the pH was approximately 7.250 mL water was added and 500 ml of ethyl acetate was added. Stirring was pursued for 20 minutes. The organic phase was separated and the aqueous layer extracted with 250 mL ethyl acetate. Drying over magnesium sulfate and concentration in a rotatory evaporator left a brownish oil (118 g, 97%) that was dried at the pump. MS: m/e=165 (M–H+).

b) 13-(4-Fluoro-benzyloxy)-phenyl]-acetic acid methyl ester (3-Hydroxy-phenyl)-acetic acid methyl ester (157 g, 610.1 mmol), was dissolved under argon in 510 mL of acetone and then potassium carbonate (109.6 g, 793.23 mmol), was added, followed 10 minutes later by 78.9 mL 4-fluorobenzyl bromide (78.9 ml, 640.6 mmol). The colorless mixture was heated under reflux (50° C.) for 48 hours at this temperature, and then cooled to room temperature. The reaction was filtered over a filter funnel, and the filtrate concentrated in a rotary evaporator to give an oil that was dissolved in 170 mL dichloromethane and 200 mL of a saturated NH₄Cl solution. The organic phase was separated and the aqueous layer extracted with dichloromethane. Drying over magnesium sulfate and concentration in a rotatory evaporator left a brownish oil that was dried at the pump (160 g, 96%). MS: m/e=275 (M+H+).

c) [5-(4-Fluoro-benzyloxy)-2-iodo-phenyl]-acetic acid methyl ester

[3-(4-Fluoro-benzyloxy)-phenyl]-acetic acid methyl ester (157.4 g, 572 mmol, 1.0) was dissolved under argon in 1.57 L of acetic acid and then of iodine (145.2 g 572.4 mmol) and silver acetate (95.5 g, 572.45 mmol) were added in portions and the reaction was stirred at room temperature overnight. The silver iodide formed in the reaction was removed by filtration and washed with acetic acid. The filtrate was poured into ice water and the precipitate collected by filtration and washed with water The solid was dissolved in ethyl acetate and the solution was washed successively with water, saturated brine, a 2M NaOH solution and a saturated sodium thiosulfate solution. Drying over magnesium sulfate and concentration in a rotatory evaporator left a viscuos oil which crystallized (209.7 g, 92%). MS: m/e=399(M–H$^+$).

d) [5-(4-Fluoro-benzyloxy)-2-iodo-phenyl]-acetaldehyde

[5-(4-Fluoro-benzyloxy)-2-iodo-phenyl)-acetic acid methyl ester (12.6 g, 31.4 mmol), was dissolved under argon in 126 mL of dichloromethane and then, at –78° C., isobutylaluminum hydride (29.1 mL, 34.8 mmol) was added dropwise. The reaction mixture was stirred at –78° C. for 6 h until the TLC indicated the end of the reaction. A saturated solution of NH$_4$Cl was added and the reaction mixture was allowed to come to room temperature. Dichloromethane was added, the organic phase was separated and the aqueous layer extracted with dichloromethane. Drying over magnesium sulfate and concentration in a rotatory evaporator gave the aldehyde (12 g, 100%) that was used in the next step without purification.

e) 2(R)-{2-[5-(4-Fluoro-benzyloxy)-2-iodo-phenyl]-ethylamino}propionamide

In a 500 ml round bottom flask equipped with a magnetic stirrer and an inert gas supply H-D-alanine-NH$_2$ HCl (4.49 g, 36.1 mmol), was dissolved under argon in 175 mL methanol and then 12 g of molecular sieves (0.4 nM), was added followed by sodium cyanoborohydride (1.65 g, 26.25 mmol). The colorless mixture was stirred for 20 minutes and a solution of [5-(4-fluoro-benzyloxy)-2-iodo-phenyl]-acetaldehyde (12.1 g, 32.8 mmol) was added in 175 mL methanol. The light yellow reaction was stirred overnight at room temperature. Filtration and a concentration in a rotatory evaporator left a solid that was purified through a Silica-gel column using hexane/ethyl acetate 1/1 and MeCl$_2$/MeOH 9/1 as eluents gave two fractions of (7.25 g, 50%) of a white solid pure and 1 g of other more impure compound that was crystallized using ethyl acetate to obtain 550 mg of a white solid (in total 7.8 g, 55% yield). MS: m/e=443.2 (M'H$^+$).

f) 2(R)-[6-(4-Fluoro-benzyloxy)-1-oxo-3,4-dihydro-1H-isoquinolin-2-yl]-propionamide The autoclave was charged under an argon flow with 2-(R)-{2-[5-(4-fluoro-benzyloxy)-2-iodo-phenyl]-ethylamino}-propionamide (7.25 g, 16.3 mmol), triethylamine (4.57 ml, 32.7 mmol), bis(triphenylphosphine) palladium II chloride (115.1 mg, 0.164 mmol) with aid of 100 ml ethyl acetate. Then the autoclave was sealed, evacuated twice under slow stirring (150 rpm) to 0.2 bar and pressurized with 8 bar of argon, then pressurized three times with 20 bar of carbon monoxide and vented, and finally pressurized with 60 bar of carbon monoxide. The reaction mixture was stirred (500 rpm) and heated at 105° C. and the carbonylation carried out at 60 bar constant total pressure for 22 h. After cooling, the autoclave was vented and the CO atmosphere was exchanged by evacuating to ca. 0.2 bar and pressurizing 8 bar of argon four times. The resulting clear solution was filtrated washing with ethyl acetate and a saturated solution of NH$_4$Cl was added and the aqueous phase was extracted in a separatory funnel with ethyl acetate and then the combined organic phases were washed with 250 ml of deionized water and reduced to a total weight of 5.1 g by rotary evaporation. Recrystallisation from 4 mL ethyl acetate/Et$_2$O ~3/1 and afterwards with 4 mL of ethyl acetate gave 4.28 g, 76% of a white solid. MS: m/e=343.2 (M+H$^+$). [α]$_D$=+141.3 (c=0.1.0941 g/100 mL) (CH$_2$Cl$_2$)

EXAMPLE 21

2(S)-[6-(4-Fluoro-benzyloxy)-1-oxo-3,4-dihydro-1H-isoquinolin-2-yl]-propionamide a) 2(S)-{2-[5-(4-Fluoro-benzyloxy)-2-iodo-phenyl]-ethylamino}propionamide As described for example 20e the title compound (500 mg, 42%) was prepared from a mixture of H-L-alanine-NH$_2$ HCl (0.370 g, 2.9 mmol), sodium cyanoborohydride (136 mg, 2.16 mmol) and a solution of [5-(4-fluoro-benzyloxy)-2-iodo-phenyl]-acetaldehyde (1 g, 2.7 mmol) in 30 mL of methanol. MS: m/e=443.2 (M+H$^+$).

b) 2(S)-[6 (4-Fluoro-benzyloxy)-1-oxo-3,4-dihydro-1H-isoquinolin-2-yl]-propionamide As described for example 20f the title compound (250 mg, 65%) was prepared from a mixture of 2-(S)-{2-[5-(4-fluoro-benzyloxy)-2-iodo-phenyl]-ethylamino}-propionamide (500 mg, 1.13 mmol), triethylamine (0.229 ml, 2.26 mmol), bis (triphenylphosphine) palladium II chloride (79 mg, 0.113 mmol) in 5 ml ethyl acetate. MS: m/e=343.2 (M+H$^+$). [α]$_D$=–145.01 (c=0.1.0482 g/100 mL) (CH$_2$Cl$_2$)

EXAMPLE 22

2(S)-[6(4-Fluoro-benzyloxy)-1-oxo-3,4-dihydro-1H-isoquinolin-2-yl]]-3-hydroxy-propionamide a) 2(S)-{2-[5-(4-Fluoro-benzyloxy)-2-iodo-phenyl]-ethylamino}3-hydroxy-propionamide As described for example 20e the title compound (880 mg, 71.7%) was prepared from a mixture of L-serine amide hydrochloride (417 mg, 2.9 mmol), sodium cyanoborohydride (136 mg, 2.16 mmol) and a solution of [5-(4-fluoro-benzyloxy)-2-iodo-phenyl]-acetaldehyde (1 g, 2.7 mmol) in 31 mL of methanol. MS: m/e=459.2 (M+H$^+$).

b) 2-(S)-[6-(4-Fluoro-benzyloxy)-1-oxo-3,4-dihydro-1H-isoquinolin-2-yl]-3-hydroxy-propionamide As described for example 20f the title compound (37 mg, 32%) was prepared from a mixture of 2(S)-[2-[5-(4-Fluoro-benzyloxy)-2-iodo-phenyl]-ethylaminol 3-hydroxy-propionamide (150 mg, 0.327 mmol), triethylamine (0.091 ml, 0.655 mmol), bis (triphenylphosphine) palladium II chloride (3.5 mg, 0.005 mmol) in 5 mL ethyl acetate. MS: m/e=359.2 (M+H$^+$).

EXAMPLE 23

2(S)-[6-(4-Fluoro-benzyloxy)-1-oxo-3,4-dihydro-1H-isoquinolin-2-yl]-4-methylsulfanyl-butyramide a) 2(S)-{2-[5-(4-Fluoro-benzyloxy)-2-iodo-phenyl]-acetylamino}-4-methylsulfanyl-butyramide As described for example 20e the title compound (648 mg, 48%) was prepared from a mixture of H-Methionine-NH$_2$ HCl (548.3 mg, 2.97 mmol), sodium cyanoborohydride (136 mg, 2.16 mmol) and a solution of [5-(4-fluoro-benzyloxy)-2-iodo-phenyl)-acetaldehyde (1 g, 2.7 mmol) in 31 mL of methanol. MS: m/e 503.2 (M+H')

b) 2(S)-[6-(4-Fluoro-benzyloxy)-1-oxo-3,4-dihydro-1H-isoquinolin-2-yl]-4-methylsulfanyl-butyramide As described for example 20f the title compound (100 mg, 76%) was prepared from a mixture of 2-(S)-{2-[5-(4-fluoro-benzyloxy)-2-iodo-phenyl]-acetylamino}-4-methylsulfanyl-butyramide (164 mg, 0.327 mmol), triethylamine (0.091 mL, 0.655 mmol), bis(triphenylphosphine) palladium II chloride (3.5 mg, 0.005 mmol) in 5 mL ethyl acetate. MS: m/e=403.4 (M+H$^+$).

EXAMPLE 24

2-(R)-[6-(4-Fluoro-benzyloxy)-1-oxo-3,4-dihydro-1H-isoquinolin-2-yl]-3-hydroxy-propionamide a) 2-(R)-{2-[5-(4-Fluoro-benzyloxy)-2-iodo-phenyl]-ethylamino}3-hydroxy-propionamide As described for example 20e the title compound (118 mg, 40%) was prepared from a mixture of D(+) serine amide hydrochloride (100 mg, 0.71 mmol), sodium cyanoborohydride (32.6 mg, 0.52 mmol) and a solution of (5-(4-fluoro-benzyloxy)-2-iodo-phenyl]-acetaldehyde (240 mg, 0.648 mmol) in 7 ml of methanol. MS: m/e=459.4 (M+H$^+$).

b) 2-(R)-[6-(4-Fluoro-benzyloxy)-1-oxo-3,4-dihydro-1H-isoquinolin-2-yl]-3-hydroxy-propionamide As described for example 20f the title compound (30 mg, 34%) was prepared from a mixture of 2-(R)-{2-[5-(4-fluoro-benzyloxy)-2-iodo-phenyl]-ethylamino}3-hydroxy-propionamide (115 mg, 0.251 mmol), triethylamine (0.070 ml, 0.502 mmol), bis (triphenylphosphine) palladium II chloride (3.5 mg, 0.005 mmol) in 4.5 ml ethyl acetate. MS: m/e=359.2 (M+H$^+$).

EXAMPLE 25

2-(S)-[6-(4-Fluoro-benzyloxy)-1-oxo-3,4-dihydro-1H-isoquinolin-2-yl]-4-methyl-pentanoic acid amide a) 2-(S)-{2-[5-(4-Fluoro-benzyloxy)-2-iodo-phenyl]-ethylamino}-4-methyl-pentanoic acid amide As described for example 20e the title compound (373 mg, 77%) was prepared from a mixture of L-leucine amide hydrochloride (188 mg, 1.13 mmol), sodium cyanoborohydride (51.6 mg, 0.821 mmol) and a solution of [5-(4-fluoro-benzyloxy)-2-iodo-phenyl]-acetaldehyde (380 mg, 1.03 mmol) in 12 mL of methanol. MS: m/e=485.2 (M+H$^+$).

b) 2-(S)-[6-(4-Fluoro-benzyloxy)-1-oxo-3,4-dihydro-1H-isoquinolin-2-yl]-4-methyl-pentanoic acid amide.

As described for example 20f the title compound (120 mg, 41%) was prepared from a mixture of 2-(S)-{2-[5-(4-fluoro-benzyloxy)-2-iodo-phenyl]-ethylamino}-4-methyl-pentanoic acid amide (370 mg, 0.764 mmol), triethylamine (0.213 mL, 1.53 mmol), bis(triphenylphosphine) palladium II chloride (5.4 mg, 0.008 mmol) in 7 mL ethyl acetate. MS: m/e=385.3 (M+H$^+$).

EXAMPLE 26

2-(S)-[6-(4-Fluoro-benzyloxy)-1-oxo-3,4-dihydro-1H-isoquinolin-2-yl]-butyramide a) 2-(S)-{2-[5-(4-Fluoro-benzyloxy)-2-iodo-phenyl]-acetylamino}-butyramide As described for example 20e the title compound (280 mg, 22%) was prepared from a mixture of L aminobutyramide HCl (411 mg, 2.97 mmol), sodium cyanoborohydride (136 mg, 2.16 mmol) and a solution of [5-(4-fluoro-benzyloxy)-2-iodo-phenyl]-acetaldehyde (1 g, 2.7 mmol) in 31 ml of methanol. MS: m/e=457.3 (M+H$^+$).

b) 2-(S)-[6 (4-Fluoro-benzyloxy)-1-oxo-3,4-dihydro-1H-isoquinolin-2-yl]-butyramide As described for example 20f the title compound (50 mg, 48%) was prepared from a mixture of 2-(S)-{2-[5-(4-fluoro-benzyloxy)-2-iodo-phenyl]-acetylamino}-butyramide (138 mg, 0.293 mmol), triethylamine (0.082 mL, 0.586 mmol), bis(triphenylphosphine) palladium II chloride (4.1 mg, 0.0059 mmol) in 2.5 mL ethyl acetate. MS: m/e=357.2 (M+H$^+$).

EXAMPLE 27

2-(R)-[6-(4-Fluoro-benzyloxy)-1-oxo-3,4-dihydro-1H-isoquinolin-2-yl]-3-phenyl-propionamide a) 2-(R)-{2-[5-(4-Fluoro-benzyloxy)-2-iodo-phenyl]-ethylamino}-3-phenyl-propionamide As described for example 20e the title compound (293 mg, 56.5%) was prepared from a mixture of H-phenylalanine-NH$_2$HCl (220.6 mg, 1.1 mmol), sodium cyanoborohydride (50.3 mg, 0.8 mmol) and a solution of [5-(4-fluoro-benzyloxy)-2-iodo-phenyl]-acetaldehyde (370 mg, 1.0 mmol) in 11.5 mL of methanol. MS: m/e=519.3 (M+H$^+$).

b) 2-(R)-[6 (4-Fluoro-benzyloxy)-1-oxo-3,4-dihydro-1H-isoquinolin-2-yl]-3-phenyl-propionamide As described for example 20f the title compound (72 mg, 32%) was prepared from a mixture of 2-(R)-{2-[5-(4-fluoro-benzyloxy)-2-iodo-phenyl]-ethylamino}-3-phenyl-propionamide (280 mg, 0.540 mmol), triethylamine (0.109 mL, 1.08 mmol), bis (triphenylphosphine) palladium II chloride (8.1 mg, 0.012 mmol) in 10 ml ethyl acetate. MS: m/e=419.3-(M+H$^+$).

EXAMPLE 28

2(S)-[6 (4-Fluoro-benzyloxy)-1-oxo-3,4-dihydro-1H-isoquinolin-2-yl]-3-methyl-butyramide a) 2-(S)-{2-[5-(4-Fluoro-benzyloxy)-2-iodo-phenyl]-ethylamino}-3-methyl-butyramide As described for example 20e the title compound (332 mg, 71%) was prepared from a mixture of H-valine-NH$_2$HCl (172.3 mg, 1.12 mmol), sodium cyanoborohydride (52 mg, 0.821 mmol) and a solution of [5-(4-fluoro-benzyloxy)-2-iodo-phenyl]-acetaldehyde (380 g, 1.03 mmol) in 12 ml of methanol. MS: m/e=471.0 (M+H$^+$).

b) 2-(S)-[6-(4-Fluoro-benzyloxy)-1-oxo-3,4-dihydro-1H-isoquinolin-2-yl]-3-methyl-butyramide As described for example 20f the title compound (210 mg, 81%) was prepared from a mixture of 2-(S)-{2-[5-(4-fluoro-benzyloxy)-2-iodo-phenyl]-ethylamino}-3-methyl-butyramide (330 mg, 0.702 mmol), triethylamine (0.142 mL, 1.403 mmol), bis (triphenylphosphine) palladium II chloride (5 mg, 0.007 mmol) in 7 mL ethyl acetate. MS: m/e=371.3-(M+H$^+$).

EXAMPLE 29

2-(S)-[6-(4-Fluoro-benzyloxy)-1-oxo-3,4-dehydro-1H-isoquinolin-2-yl]-3-phenyl-propionamide a) 2-(S)-(2-(5-(4-Fluoro-benzyloxy)-2-iodo-phenyl]-ethylamino]-3-phenyl-propionamide As described for example 20e the title compound (171 mg, 33.5%) was prepared from a mixture of L-phenylalanine amide (180 mg, 1.1 mmol), sodium cyanoborohydride (50.3 mg, 0.8 mmol) and a solution of [5-(4-fluoro-benzyloxy)-2-iodo-phenyl]-acetaldehyde (370 mg, 1.0 mmol) in 11.5 ml of methanol. MS: m/e=519.2 (M+H$^+$).

b) 2-(S)-[6-(4-Fluoro-benzyloxy)-1-oxo-3,4-dihydro-1H-isoquinolin-2-yl]-3-phenyl-propionamide As described for example 20f the title compound (43 mg, 31%) was prepared from a mixture of 2-(S)-{2-[5-(4-Fluoro-benzyloxy)-2-iodo-phenyl]-ethylamino}-3-phenyl propionamide (175 mg, 0.338 mmol), triethylamine (0.068 mL, 0.675 mmol), bis (triphenylphosphine) palladium II chloride (5.1 mg, 0.007 mmol) in 7 mL ethyl acetate. MS: m/e=419.3-(M+H$^+$).

EXAMPLE 30

2-[6-(4-Fluoro-benzyloxy)-1-oxo-3,4-dihydro-1H-isoquinolin-2-yl]-isobutyramide a) 2-[6-(4-Fluoro-benzyloxy)-1-oxo-3,4-dihydro-1H-isoquinolin-2-yl]-2-methyl-propionic acid ethyl ester The 2-[6-(4-fluoro-benzyloxy)-1-oxo-3,4-dihydro-1H-isoquinolin-2-yl]-propionic acid ethyl ester (Example 10b, 365 mg, 0.983 mmol) was solved in THF (3.5 ml) and at −78° C. was added potassium bis(trimethylsilyl)amide (7.8 mL, 3.9 mmol), followed 15 min later by methyl iodide (0.368 mL, 5.89 mmol). The reaction mixture was stirred at −78° C. for 5 hours. Ammonium chloride was added and the reaction extracted with dichloromethane. The organic phases were dried over sodium sulfate and evaporated. The crude product was purified by column chromatography (hexane to hexane/ethyl acetate 1:1) to give 288 mg (76%) of the product. MS: m/e=386.2 (M+H$^+$).

b) 2-[6 (4-Fluoro-benzyloxy)-1-oxo-3,4-dihydro-1H-isoquinolin-2-yl]-2-methyl-propionic acid A mixture of the 2-[6-(4-fluoro-benzyloxy)-1-oxo-3,4-dihydro-1H-isoquinolin-2-yl]-2-methyl-propionic acid ethyl ester (220 mg, 0.571 mmol) and lithium hydroxide (274 mg, 11.41 mmol) in water and dioxane (1:1 v:v, 5 mL) was stirred at 50° C. overnight. The dioxane was evaporated and the mixture acidified to pH 3–4 with 0.1 N HCl. After extraction with ethyl acetate, drying of the organic layer with magnesium sulfate, filtration and evaporation a white solid was obtained (196 g, 96%). MS: m/e 356.1 (M−H+).

c) 2-[6-(4-Fluoro-benzyloxy)-1-oxo-3,4-dihydro-1H-isoquinolin-2-yl]-isobutyramide A mixture of 2-[6-(4-fluoro-benzyloxy)-1-oxo-3,4-dihydro-1H-isoquinolin-2-yl]-2-methyl-propionic acid (175 mg, 0.490 mmol) and benzotriazol-1-yloxy-tripyrrolidino-phosphonium hexafluorophosphate (PyBOP, 382 mg, 0.735 mmol) and butanol (99.3 mg, 0.735 mmol) in N,N'-dimethylformamide (6 mL) was stirred at room temperature for 10 min. Ammonium chloride (52.4 mg, 0.979 mmol) was added and the mixture was stirred 2 h. Water was added and the mixture was extracted with ethyl acetate. The organic phase is successively washed with sodium hydrogencarbonate 10% and MCl 0.1M. Drying and evaporation of the solvent left a solid which was recrystallised with ethyl acetate and ether (120 mg, 69%). MS: m/e=357.2-(M+H$^+$).

EXAMPLE 31

2-[6 (2-Fluoro-benzyloxy)-1-oxo-3,4-dihydro-1H-isoquinolin-2-yl]-propionamide a) 2-(6-Hydroxy-1-oxo-3,4-dihydro-1H-isoquinolin-2-yl)-propionamide 2-[6-(4-Fluoro-benzyloxy)-1-oxo-3,4-dihydro-1H-isoquinolin-2-yl]-propionamide (example 10) (3 g, 8.76 mmol) was solved in dry ethanol (150 mL) and under an argon flow, palladium on charcoal 10% was added (93 mg, 0.0876 mmol). The argon was evacuated and replaced by hydrogen. The reaction mixture was stirred overnight and after evacuation of the hydrogen and replacement by argon the system was opened and the reaction filtrated to remove the palladium and concentrated. After concentration the compound was obtained as a white solid (2.17 g, 100%). MS: m/e=232.8 (M−H+).

b) 2-[6-(2-Fluoro-benzyloxy)-1-oxo-3,4-dihydro-1H-isoquinolin-2-yl]-propionamide 2-(6-Hydroxy-1-oxo-3,4-dihydro-1H-isoquinolin-2-yl)-propionamide (50 mg, 0.213 mmol), was solved in dry acetone (1 mL) and potassium carbonate (38.3 mg, 0.276 mmol) was added followed by 2-fluorobenzyl bromide (42.36 mg, 0.224 mmol). The mixture was stirred overnight. Water was added and a precipitate appeared. The precipitated was filtrated and the title compound was obtained as a white solid (58 mg, 79%). MS: m/e=343.2 (M+H$^+$).

EXAMPLE 32

2-[6-(3-Chloro-benzyloxy)-1-oxo-3,4-dihydro-1H-isoquinolin-2-yl]-propionamide

As described for example 31b, 2-(6-hydroxy-1-oxo-3,4-dihydro-1H-isoquinolin-2-yl)-propionamide (50 mg, 0.213 mmol) was converted to the title compound (41 mg, 54%) using ethyl-3-chlorobenzyl bromide instead of 2-fluorobenzyl bromide. MS: m/e=359.1 (M+H$^+$).

EXAMPLE 33

2(R)-[6-(2,6-Difluoro-benzyloxy)-1-oxo-3,4-dihydro-1H-isoquinolin-2-yl]-propionamide a) 2(R)-(6-Hydroxy-1-oxo-3,4-dihydro-1H-isoquinolin-2-yl)-propionamide As described for example 31a, 2(R)-[6-(4-fluoro-benzyloxy)-1-oxo-3,4-dihydro-1H-isoquinolin-2-yl]-propionamide (1.54 g, 4.49 mmol) was converted to the title compound (0.894 mg, 84%). MS: m/e=232.8 (M−H+).

b) 2(R)-[6-(2,4-Difluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (40 mg, 0.171 mmol) was converted to the title compound (40 mg, 65%) using 2,4-difluorobenzyl bromide instead of 2-fluorobenzyl bromide. MS: m/e=361.3 (M+H$^+$).

EXAMPLE 34

2(R)-[6-(2-Fluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (40 mg, 0.171 mmol) was converted to the title compound (49 mg, 83%) using 2-fluorobenzyl bromide. MS: m/e=343.2 (M+H$^+$).

EXAMPLE 35

2(R)-[6-(2,3-Difluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (40 mg, 0.171 mmol) was converted to the title compound (40 mg, 65%) using 2,3-difluorobenzyl bromide instead of 2-fluorobenzyl bromide. MS: m/e=361.2 (M+H$^+$).

EXAMPLE 36

2(R)-[6-(2,6-Difluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (40 mg, 0.171 mmol) was converted to the title compound (20 mg, 33%) using 2,6-difluorobenzyl bromide instead of 2-fluorobenzyl bromide. MS: m/e=361.3 (M+H$^+$).

EXAMPLE 37

2(R)-[6-(3-Cyano-benzyloxy)-1-oxo-3,4-dihydro-1H-isoquinolin-2-yl]-propionamide

As described for example 31b, 2(R)-(6-hydroxy-1-oxo-3,4-dihydro-1H-isoquinolin-2-yl)-propionamide (40 mg, 0.171 mmol) was converted to the title compound (50 mg, 84%) using α-bromo-m-toluolnitrile instead of 2-fluorobenzyl bromide. MS: m/e=350.3 (M+H$^+$).

EXAMPLE 38

2(R)-[6-(3,4-Difluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (80 mg, 0.342 mmol) was converted to the title compound (90 mg, 73%) using 3,4-difluorobenzyl bromide instead of 2-fluorobenzyl bromide. MS: m/e=361.3 (M+H$^+$).

EXAMPLE 39

2(R)-[6-(3,5-Difluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (40 mg, 0.171 mmol) was converted to the title compound (53 mg, 86%) using 3,5-difluorobenzyl bromide instead of 2-fluorobenzyl bromide. MS: m/e=361.2 (M+H$^+$).

EXAMPLE 40

2(R)-[6-(3-Fluoro-benzyloxy)-1-oxo-3,4-dihydro-1H-isoquinolin-2-yl]-propionamide As described for example 31b, 2(R)-(6-hydroxy-1-oxo-3,4-dihydro-1H-isoquinolin-2-yl)-propionamide (80 mg, 0.342 mmol) was converted to the title compound (97 mg, 83%) using 3-fluorobenzyl bromide instead of 2-fluorobenzyl bromide. MS: m/e=343.2 (M+H$^+$).

EXAMPLE 41

2(S)-[6-(3-Fluoro-benzyloxy)-1-oxo-3,4-dihydro-1H-isoquinolin-2-yl]-propionamide a) 2(S)-(6-Hydroxy-1-oxo-3,4-dihydro-1H-isoquinolin-2-yl)-propionamide As described for example 31a, 2(S)-[6-(4-fluoro-benzyloxy)-1-oxo-3,4-dihydro-1H-isoquinolin-2-yl]-propionamide (200 mg, 0.584 mmol) was converted to the title compound (0.130 mg, 100%). MS: m/e=235.3 (M−H$^+$).

b) 2(S)-[6 (3-Fluoro-benzyloxy)-1-oxo-3,4-dihydro-1H-isoquinolin-2-yl]-propionamide As described for example 31b, 2(S)-(6-hydroxy-1-oxo-3,4-dihydro-1H-isoquinolin-2-yl)-propionamide (45 mg, 0.192 mmol) was converted to the title compound (66 mg, 100%) using 3-fluorobenzyl bromide instead of 2-fluorobenzyl bromide. MS: m/e=343.2 (M+H$^+$).

EXAMPLE 42

2(S)-[6 (3,4-Difluoro-benzyloxy)-1-oxo-3,4-dihydro-1H-isoquinolin-2-yl]-propionamide As described for example 31b, 2(S)-(6-hydroxy-1-oxo-3,4-dihydro-1H-isoquinolin-2-yl)-propionamide (27 mg, 0.115 mmol) was converted to the title compound (20 mg, 48%) using 3,4-difluorobenzyl bromide instead of 2-fluorobenzyl bromide. MS: m/e=361.3 (M+H$^+$).

EXAMPLE 43

6-(3-Fluoro-benzyloxy)-1,2,3,4-tetrahydro-isoquinoline

A mixture of 6-(3-fluoro-benzyloxy)-3,4-dihydro-2H-isoquinolin-1-one (1.2 g, 4.423 mmol) and lithium aluminum hydride (0.337 g, 8,84 mmol) in tetrahydrofuran (24 ml) was heated to 60° C. for 8 h. Water was added and an 15% aqueous solution of sodium hydroxide and the mixture was extracted with ethylacetate. After drying of the organic layer with MgSO$_4$, filtration and evaporation, an oil was obtained (1.14 g, 99%). MS: m/e 258.0 (M+H$^+$).

EXAMPLE 44

2-[6-(3-Fluoro-benzyloxy)-3,4-dihydro-1H-isoquinolin-2-yl]-propionamide

To a mixture of 6-(3-fluoro-benzyloxy)-1,2,3,4-tetrahydro-isoquinoline (0.200 g, 0.78 mmol) and potassium carbonate (0.215 mg, 1.56 mmol) in acetone, 2-bromo-propionamide (0.142 mg, 0.936 mmol) was added and the resulting mixture was stirred overnight at room temperature. The mixture, after filtration and evaporation, was purified by chromatography (SiO$_2$, hexane/Et$_2$O 3:2 v:v) to give the title compound as a white solid (0.189 g, 74%). MS: m/e=329.3 (M+H$^+$).

EXAMPLE 45

2-[6-(3-Fluoro-benzyloxy)-3,4-dihydro-1H-isoquinolin-2-yl]-propionic acid ethyl ester As described for example 44, 6-(3-fluoro-benzyloxy)-1,2,3,4-tetrahydro-isoquinoline (0.300 g, 1.16 mmol) was converted to the title compound (0.338 g, 81%) using ethyl-2-bromopropionate (0.182 mL, 1.39 mmol) instead of 2-bromopropion-amide. MS: m/e=358.3 (M+H$^+$).

EXAMPLE 46

2-[6-(4-Fluoro-benzyloxy)-3,4-dihydro-1H-isoquinolin-2-yl]-acetamide a) 6-(4-Fluoro-benzyloxy)-1,2,3,4-tetrahydro-isoquinoline As described for example 43, the title compound (1.86 g, 98%) was prepared from a mixture of 6-(4-fluoro-benzyloxy)-3,4-dihydro-2H-isoquinolin-1-one (2 g, 7.37 mmol) and lithium aluminum hydride (0.559 g, 14.74 mmol) in tetrahydrofuran. MS: m/e=258.0 (M+H$^+$)

b) 2-[6-(4-Fluoro-benzyloxy)-3,4-dihydro-1H-isoquinolin-2-yl]-acetamide

As described for example 44, 6-(4-fluoro-benzyloxy)-1,2,3,4-tetrahydro-isoquinoline (0.300 g, 1.16 mmol) was converted to the title compound (0.338 g, 81%) using 2-bromoacetamide (0.191 mg, 1.39 mmol) instead of 2-bromopropionamide. MS: m/e=315.3 (M+H$^+$).

EXAMPLE 47

2-[6-(3-Fluoro-benzyloxy)-3,4-dihydro-1H-isoquinolin-2-yl]-acetamide

As described for example 44, 6-(3-fluoro-benzyloxy)-1,2,3,4-tetrahydro-isoquinoline (0.300 g, 1.16 mmol) was converted to the title compound (0.218 g, 60%) using 2-bromoacetamide (0.191 mg, 1.39 mmol) instead of 2-bromopropionamide. MS: m/e=315.3 (M+H$^+$).

EXAMPLE 48

3-[6 (4-Fluoro-benzyloxy)-3,4-dihydro-1H-isoquinolin-2-yl]-propionamide

As described for example 44, 6-(4-fluoro-benzyloxy)-1,2,3,4-tetrahydro-isoquinoline (0.100 g, 0.39 mmol) was converted to the title compound (0.099 g, 77%) using 3-bromo-propionamide (0.071 g, 0.47 mmol) instead of 2-bromopropionamide. MS: m/e=329.4 (M+H$^+$).

EXAMPLE 49

2-[6-(4-Fluoro-benzyloxy)-3,4-dihydro-1H-isoquinolin-2-yl]-propionamide

As described for example 44, 6-(4-fluoro-benzyloxy)-1,2,3,4-tetrahydro-isoquinoline (0.200 g, 0.78 mmol) was converted to the title compound (0.170 g, 67%) using 2-bromopropionamide (0.142 g, 0.93 mmol). MS: m/e=329.3 (M+H$^+$).

EXAMPLE 50

3-[6-(3-Fluoro-benzyloxy)-3,4-dihydro-1H-isoquinolin-2-yl]-propionamide

As described for example 44, 6-(3-fluoro-benzyloxy)-1,2,3,4-tetrahydro-isoquinoline (0.100 g, 0.39 mmol) was converted to the title compound (0.089 g, 70%) using 3-bromopropionamide (0.071 g, 0.47 mmol) instead of 2-bromopropionamide. MS: m/e=329.3 (M+H$^+$).

EXAMPLE 51

2-(2-Ethoxy-ethyl)-6-(3-fluoro-benzyloxy)-1,2,3,4-tetrahydro-isoquinoline

As described for example 44, 6-(3-fluoro-benzyloxy)-1,2,3,4-tetrahydro-isoquinoline (0.100 g, 0.39 mmol) was converted to the tide compound (0.075 g, 59%) using 2-bromoethyl ethyl ether (0.072,g, 0.47 mmol) instead of 2-bromopropionamide. MS: m/e=330.4 (M+H$^+$).

EXAMPLE 52

6-(4-Fluoro-benzyloxy)-2-(2-methoxy-ethyl)-1,2,3,4-tetrahydro-isoquinoline

As described for example 44, 6-(4-fluoro-benzyloxy)-1,2,3,4-tetrahydro-isoquinoline (0.100 g, 0.39 mmol) was converted to the title compound (0.054 g, 44%) using 2-bromoethyl methyl ether (0.044 mL, 0.47 mmol) instead of 2-bromo-propionamide. MS: m/e=316.3 (M+H$^+$).

EXAMPLE 53

6-(4-fluoro-benzyloxy)-2-(4,4,4-trifluoro-butyl)-1,2,3,4-tetrahydro-isoquinoline As described for example 44, 6-(4-fluoro-benzyloxy)-1,2,3,4-tetrahydro-isoquinoline (0.100 g, 0.39 mmol) was converted to the title compound (0.065 g, 46%) using 1-bromo-4,4,4-trifluorobutane (0.089 g, 0.47 mmol) instead of 2-bromopropionamide. MS: m/e=368.3 (M+H$^+$).

EXAMPLE 54

6-(4-Fluoro-benzyloxy)-2-(tetrahydro-furan-2-ylmethyl)-1,2,3,4-tetrahydro-isoquinoline As described for example 44,6-(4-fluoro-benzyloxy)-1,2,3,4-tetrahydro-isoquinoline (0.100 g, 0.39 mmol) was converted to the title compound (0.029 g, 22%) using tetrahydrofurfuryl bromide (0.077 g, 0.47 mmol) instead of 2-bromopropion-amide. MS: m/e=342.3 (M+H$^+$).

EXAMPLE 55

2-(2-Ethoxy-ethyl)-6-(4-fluoro-benzyloxy)-1,2,3,4-tetrahydro-isoquinoline

As described for example 44, 6-(4-fluoro-benzyloxy)-1,2,3,4-tetrahydro-isoquinoline (0.100 g, 0.39 mmol) was converted to the title compound (0.048 g, 39%) using 2-bromoethyl ethyl ether (0.072 g, 0.47 mmol) instead of 2-bromopropionamide. MS: m/e=330.6 (M+H$^+$).

EXAMPLE 56

3-[6-(4-Fluoro-benzyloxy)-3,4-dihydro-1H-isoquinolin-2-yl]-2-S-methyl-propionic acid methyl ester As described for example 21, 6-(4-fluoro-benzyloxy)-1,2,3,4-tetrahydro-isoquinoline (0.100 g, 0.39 mmol) was converted to the title compound (0.022 g, 6%) using methyl (S)-3-bromo-2-methylpropionate (0.084 g, 0.47 mmol) instead of 2-bromopropionamide. MS: n/e=358.3 (M+H$^+$).

EXAMPLE 57

2-(R)-[6 (4-Fluoro-benzyloxy)-1,3-dioxo-3,4-dihydro-1H-isoquinolin-2-yl 1-propionamide a) [5-(4-Fluoro-benzyloxy)-2-iodo-phenyl]-acetic acid A mixture of the [5-(4-fluoro-benzyloxy)-2-iodo-phenyl]-acetic acid methyl ester (example 20c, 3 g, 7.49 mmol) and lithium hydroxide (215 mg, 8.99 mmol) in water and THF (1:1 v:v, 40 mL) was stirred at room temperature for 2 h. The THF was evaporated and the mixture acidified to pH 3–4 with 0.1N HCl. After extraction with ethyl acetate, drying of the organic layer with magnesium sulfate, filtration and evaporation a white solid was obtained (2.9 g, 100%). MS: m/e=384.9 (M–H$^+$).

b) 2-(R)-{2-[5-(4-Fluoro-benzyloxy)-2-iodo-phenyl]-acetylamino}-propionamide

A mixture of [5-(4-fluoro-benzyloxy)-2-iodo-phenyl]-acetic acid (300 mg, 0.777 mmol) and 1,1'-carbonyl-diimidazole (138 mg, 0.855 mmol) in N,N'-dimethyl-formamide (2 mL) was stirred at 50° C. for 0.5 h. H-D-alanine-NH$_2$HCl (145 mg, 1.16 mmol) was added and the mixture was stirred at 50° C. for 2 h. Water was added and the product precipitated. The solid was filtrated (317 mg, 89.5%). MS: m/e=457.3 (M+H$^+$).

c) 2-(R)-[6-(4-Fluoro-benzyloxy)-1,3-dioxo-3,4-dihydro-1H-isoquinolin-2-yl]-propionamide As described for example 20f, the title compound (10 mg, 25%) was prepared from a mixture of 2-(R)-{2-[5-(4-Fluoro-benzyloxy)-2-iodo-phenyl]-acetylamino}-propionamide (50 mg, 0.109 mmol), triethylamine (0.030 mL, 0.218 mmol), bis (triphenylphosphine) palladium II chloride (1.5 mg, 0.0022 mmol) in 1 mL ethyl acetate. MS: m/e=357.2 (M+H$^+$).

EXAMPLE 58

2(S)-[6-(4-Fluoro-benzyloxy)-1,3-dioxo-3,4-dihydro-1H-isoquinolin-2-yl]-propionamide a) 2-(S)-{2-[5-(4-Fluoro-benzyloxy)-2-iodo-phenyl]-acetylamino}-propionamide A mixture of (5-(4-fluoro-benzyloxy)-2-iodo-phenyl]-acetic acid (example 45a, 355 mg, 0.919 mmol) and 1,1'-carbonyl-diimidazole (164 mg, 1.01 mmol) in N,N'-dimethylformamide (2 mL) was stirred at 50° C. for 1.5 h. H-L-alanine-NH$_2$HCl (145 mg, 1.16 mmol) was added and the mixture was stirred at 50° C. overnight. Water was added and the product precipitated. The solid was filtrated (368 mg, 88%). MS: m/e=457.2 (M+H$^+$).

b) 2(S)-[6-(4-Fluoro-benzyloxy)-1,3-dioxo-3,4-dihydro-1H-isoquinolin-2-yl]-propionamide As described for example 20f the title compound (43 mg, 10%) was prepared from a mixture of 2(S)-{2-[5-(4-Fluorobenzyloxy)-2-iodo-phenyl]-acetylamino}-propionamide (555 mg, 1.22 mmol), triethylamine (0.383 ml, 2.43 mmol), bis (triphenylphosphine) palladium II chloride (17 mg, 0.0244 mmol) in 10 ml ethyl acetate. MS: m/e=357.1 (M+H$^+$).

EXAMPLE 59

2(S)-[6-(4-Fluoro-benzyloxy)-3-oxo-3,4-dihydro-1H-isoquinolin-2-yl]-propionamide a) 5-(4-Fluoro-benzyloxy)-indan-1-one The 5-hydroxy-1-indanone (20 g, 134.9 mmol) was solved in dry in N,N'-dimethylformamide (120 mL) and the 4-fluorobenzyl bromide (18.2 mL, 148.4 mmol) was added followed by potassium carbonate anhydrous (24.2 g, 175.4 mmol) and the mixture was stirred for 12 h to 110 IC. Water was added and the resulting precipitate was filtrated and dried (34.6 g, 100%). MS: m/e=256.1 (M$^+$).

b) 5-(4-Fluoro-benzyloxy)-indan-1,2-dione 2-oxime

Isoamyl nitrite (4.05 mL, 29.2 mmol) was added to a suspension of 5-(4-fluoro-benzyloxy)-indan-1-one (15 g, 58.5 mmol) in methyl cellulose (210 mL) and HCl (conc) (15.6 mL, 187 mmol) at room temperature. After some minutes (~10) a solid appears and another portion of the isoamyl nitrite (4.05 mL, 29.2 mol) was added. The mixture was stirred for further 30 minutes, poured on ice water and the product was filtrated, washed well with water and diluted EtOH and dried at the pump (15.2 g, 91%). MS: m/e =284.1 (M−H).

c) 2-Carboxymethyl-4-(4-fluoro-benzyloxy)-benzoic acid 5-(4-Fluoro-benzyloxy)-indan-1,2-dione 2-oxime (6 g, 22.2 mmol) is solved in a 10% aqueous solution of NaOH (60 mL, 155.8 mmol). The mixture is heated at 60° C. and p-toluenesulfonyl chloride (21.24 g, 111.4 mmol) is added slowly during one hour. The reaction mixture is refluxed 4 h. The reaction is acidified with concentrate HCl and the precipitate is filtered and dried at the pump (4.42 g, 65%). MS: m/e=303.0 (M−H).

d) 6-(4-Fluoro-benzyloxy)-isochroman-1,3-dione

The 2-Carboxymethyl-4-(4-fluoro-benzyloxy)-benzoic acid (3.4 g, 11.1 mmol) is suspended in acetylchloride (23.8 mL, 33.5 mmol) and refluxed for 4 h. Then the light brown precipitate is filtered off and washed with ether. The mother liquid is concentrated and suspended in cold diethylether and the rest of the compound is filtered again (2.85 g, 90%). MS: m/e=286.1 (M$^+$).

e) 4-(4-Fluoro-benzyloxy)-2-methoxycarbonylmethyl-benzoic acid

The 6-(4-fluoro-benzyloxy)-isochroman-1,3-dione (1.3 g, 4.5 mmol) is solved in methanol (10 mL) and heated to 90° C. in a dosed tube. After 2 h the precipitated was filtered (1.2 g, 83%). MS: m/e=316.7 (M−H).

f) [5-(4-Fluoro-benzyloxy)-2-hydroxymethyl-phenyl]-acetic acid methyl ester

The 4-(4-fluoro-benzyloxy)-2-methoxycarbonylmethyl-benzoic acid (1.15 g, 3.6 mmol) is solved in THF (28 mL) and borane-dimethylsulfide complex is added (0.69 mL, 7.26 mmol) at 0° C. The reaction is stirred for 2 hours at room temperature and more borane-dimethylsulfide complex (0.69 mL, 7.26 mmol) is added at 0° C. The reaction mixture was stirred at room temperature for 7 h. Methanol was added very slowly and the mixture stirred 20 min. Filtration and concentration in a rotatory evaporator left a solid that was purified through a Silica-gel column using hexane/ethyl acetate 3/1 to 1/2 as eluents (0.927 g, 71.4%). MS: m/e=304 (M$^+$).

g) [5-(4-Fluoro-benzyloxy-2-formyl-phenyl]-acetic acid methyl ester

[5-(4-Fluoro-benzyloxy)-2-hydroxymethyl-phenyl)-acetic acid methyl ester (0.850 g, 2.79 mmol) is solved in CHCl$_3$ (25 mL) and MnO$_2$ (2.15 g, 22.34 mmol) is added and the mixture refluxed for 2 h and more MnO$_2$ (0.270 g, 2.79 mmol) was added and the mixture refluxed again for 30 min. Filtration and evaporation of the chloroform gave the aldehyde (0.746 g, 85%) that was used in the next step without purification. MS: m/e=304 (M$^+$).

h) [2-[(1(S)-Carbamoyl-ethylamino)-methyl]-5-(4-fluoro-benzyloxy)-phenyl]-acetic acid methyl ester H-L-Alanine-NH$_2$ HCl (0.222 g, 1.78 mmol), was dissolved under argon in 3 mL of methanol and then 0.500 g of molecular sieves (0.4 nM) was added followed by sodium cyanoborohydride (0.075 g, 1.19 mmol). The mixture was stirred for 20 minutes and a solution of (5-(4-fluoro-benzyloxy)-2-formyl-phenyl]-acetic acid methyl ester (0.450 g, 1.48 mmol) was added in 3 mL methanol. The light yellow reaction was stirred overnight at room temperature. Filtration and concentration in a rotatory evaporator left a solid that was purified through a silica-gel column using hexane/ethyl acetate 111 and MeCl$_2$/MeOH 911 as eluents gave (0.160 g, 29%) of a white solid. MS: m/e=375.4 (M+H$^+$).

i) 2-(S)-[6-(4-Fluoro-benzyloxy)-3-oxo-3,4-dihydro-1H-isoquinolin-2-yl]-propionamide

[2-[(1(S)-Carbamoyl-ethylamino)-methyl]-5-(4-fluoro-benzyloxy)-phenyl]-acetic acid methyl ester (0.150 g, 0.401 mmol) is refluxed in toluene at 140° C. with a Deam-Stark trap to remove the methanol formed in the reaction. After 5 h the product is obtained. The toluene is removed by evaporation and the compound is crystallized in ether (0.115 g, 84%). MS: m/e=343.4 (M+H$^+$).

EXAMPLE 60

2-(R)-[6(4-Fluoro-benzyloxy)-3-oxo-3,4-dihydro-1H-isoquinolin-2-yl 1-propionamide a) [2-[1-(R)-Carbamoyl-ethylamino)-methyl]-5-(4-fluoro-benzyloxy)-phenyl]-acetic acid methyl ester As described for example 59h, the title compound (249 mg, 30%) was prepared from a mixture of 15-(4-fluoro-benzyloxy)-2-formyl-phenyl]-acetic acid methyl ester (680 mg, 2.25 mmol), H-D-alanine-NH$_2$HCl (0.354 g, 2.8 mmol), 500 mg of molecular sieves (0.4 nM) and sodium cyanoborohydride (0.113 g, 1.8 mmol) in 5 mL of methanol. MS: m/e=375.4 (M+H$^+$).

b) 2-(R)-[6-(4-Fluoro-benzyloxy)-3-oxo-3,4-dihydro-1H-isoquinolin-2-yl]-propionamide As described for example 59i, the title compound (0.158 g, 74%) was prepared from [2-[(1-(R)-carbamoyl-ethylamino)-methyl]-5-(4-fluoro-benzyloxy)-phenyl]-acetic acid methyl ester. MS: m/e=343.4 (M+H$^+$).

EXAMPLE A

Tablets of the following composition are produced in a conventional manner:

| mg/Tablet | |
| --- | --- |
| Active ingredient | 100 |
| Powdered lactose | 95 |
| White corn starch | 35 |
| Polyvinylpyrrolidone | 8 |

-continued

| | mg/Tablet |
|---|---|
| Na carboxymethylstarch | 10 |
| Magnesium stearate | 2 |
| Tablet weight | 250 |

EXAMPLE B

Tablets of the following composition are produced in a conventional manner.

| | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

| | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

EXAMPLE D

An injection solution may have the following composition and is manufactured in usual manner:

| | | |
|---|---|---|
| Active substance | 1.0 | mg |
| 1 N HCl | 20.0 | µl |
| acetic acid | 0.5 | mg |
| NaCl | 8.0 | mg |
| phenol | 10.0 | mg |
| 1 N NaOH | q.s. ad pH 5 | |
| H$_2$O | q.s. ad 1 ml | |

What is claimed is:

1. A compound of formula

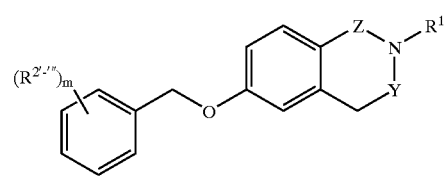

(I)

wherein
Y is >C=O or —CH$_2$—;
Z is >C=O or —CH$_2$—;
R$^1$ is hydrogen or is a group of formula

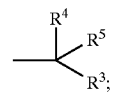

(a)

R$^{2\text{-}1\text{-}111}$ each R$^2$ is independently selected from halogen, halogen-(C$_1$–C$_6$)-alkyl, cyano, C$_1$–C$_6$-alkoxy or halogen-(C$_1$–C$_6$)-alkoxy,
R$^3$ is selected from —(CH$_2$)$_n$—CO—NR$^6$R$^7$,
—(CH$_2$)$_n$—CN,
—(CH$_2$)$_p$—OR$^8$,
—(CH$_2$)$_n$—NR$^6$R$^7$,
—(CH$_2$)$_n$—CF$_3$,
—(CH$_2$)$_n$—NH—COR$^9$,
—(CH$_2$)$_n$-tetrahydrofuranyl,
—(CH$_2$)$_p$—SR$^8$,
—(CH$_2$)$_p$—SO—R$^9$, or
—(CH$_2$)$_n$—CS—NR$^5$R$^6$;
R$^4$ is hydrogen, C$_1$–C$_6$-alkyl, —(CH$_2$)$_p$—OR$^8$, —(CH$_2$)$_p$—SR$^8$, or benzyl;
R$^5$ is hydrogen, C$_1$–C$_6$-alkyl, —(CH$_2$)$_p$—OR$^8$, —(CH$_2$)$_p$—SR$^8$, or benzyl;
R$^6$ and R$^7$ are each independently selected from hydrogen or C$_1$–C$_6$-alkyl;
R$^8$ is hydrogen or C$_1$–C$_6$-alkyl;
R$^9$ is C$_1$–C$_6$-alkyl;
m is 1, 2 or 3;
n is 0, 1 or 2; and
p is 1 or 2;
or the pharmaceutically acceptable salts thereof.

2. The compound of claim 1, wherein
Y is >C=O or —CH$_2$—;
Z is >C=O or —CH$_2$—;
R$^1$ is hydrogen or is a group of formula

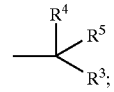

(a)

R$^{2\text{-}1\text{-}111}$ each R$^2$ is independently selected from halogen, halogen-(C$_1$–C$_6$)-alkyl, cyano, C$_1$–C$_6$-alkoxy or halogen-(C$_1$–C$_6$)-alkoxy,
R$^3$ is selected from —(CH$_2$)$_n$—CO—NR$^6$R$^7$
—(CH$_2$)$_n$—CN,
—(CH$_2$)$_p$—OR$^8$,
—(CH$_2$)$_n$—NR$^6$R$^7$, —(CH$_2$)$_n$—CF$_3$,
—(CH$_2$)$_n$—NH—COR$^9$,
—(CH$_2$)$_n$-tetrahydrofuranyl,
—(CH$_2$)$_p$—SR$^8$,
—(CH$_2$)$_p$—SO—R$^9$, or
—(CH$_2$)$_n$—CS—NR$^5$R$^6$;

R$^4$ is hydrogen or C$_1$–C$_6$-alkyl;

R$^5$ is hydrogen or C$_1$–C$_6$-alkyl;

R$^6$ and R$^7$ are each independently selected from hydrogen or C$_1$–C$_6$-alkyl;

R$^8$ is hydrogen or C$_1$–C$_6$-alkyl;

R$^9$ is C$_1$–C$_6$-alkyl;

m is 1, 2 or 3;

n is 0, 1 or 2; and p is 1 or 2;

or the pharmaceutically acceptable salts thereof.

3. The compound of claim 1, wherein at least one of Y or Z is >C=O.

4. The compound of claim 1, wherein either R$^1$ or R$^5$ is C$_1$–C$_6$-alkyl.

5. A compound of formula

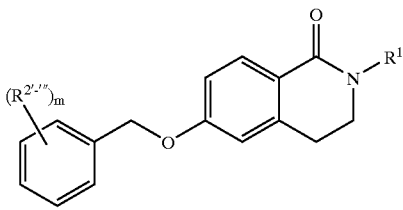

I-A wherein

R$^1$ is hydrogen or is a group of formula

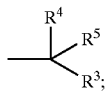

(a)

R$^{2^{1\text{-}111}}$ each R$^2$ is independently selected from halogen, halogen-(C$_1$–C$_6$)-alkyl, cyano, C$_1$–C$_6$-alkoxy or halogen-(C$_1$–C$_6$)-alkoxy, R$^3$ is selected from —(CH$_2$)$_n$—CO—NR$^6$R$^7$,
—(CH$_2$)$_n$—CN,
—(CH$_2$)$_p$—OR$^8$,
—(CH$_2$)$_n$—NR$^6$R$^7$,
—(CH$_2$)$_n$—CF$_3$,
—(CH$_2$)$_n$—NH—COR$^9$,
—(CH$_2$)$_n$-tetrahydrofuranyl,
—(CH$_2$)$_p$—SR$^8$,
—(CH$_2$)$_p$—SO—R$^9$, or
—(CH$_2$)$_n$—CS—NR$^5$R$^6$;

R$^4$ is hydrogen, C$_1$–C$_6$-alkyl, —(CH$_2$)$_p$—OR$^8$, —(CH$_2$)$_p$—SR$^8$, or benzyl;

R$^5$ is hydrogen, C$_1$–C$_6$-alkyl, —(CH$_2$)$_p$—OR$^8$, —(CH$_2$)$_p$—SR$^8$, or benzyl;

R$^6$ and R$^7$ are each independently selected from hydrogen or C$_1$–C$_6$-alkyl;

R$^8$ is hydrogen or C$_1$–C$_6$-alkyl;

R$^9$ is C$_{1\text{-}6}$-alkyl;

m is 1, 2 or 3;

n is 0, 1 or 2; and p is 1 or 2;

or the pharmaceutically acceptable salts thereof.

6. The compound of claim 5, wherein R$^1$ is a group of formula (a); R$^3$ is —(CH$_2$)$_n$—CO—NR$^6$R$^7$, —(CH$_2$)$_n$—CN or —(CH$_2$)$_p$—OR$^8$; R$^6$ and R$^7$ are each independently selected from hydrogen or C$_1$–C$_6$-alkyl; R$^8$ is hydrogen or C$_1$–C$_6$-alkyl; n is 0, 1 or 2; and p is 1 or 2.

7. The compound of claim 6, wherein R$^3$ is —(CH$_2$)$_n$—CO—NR$^6$R$^7$; R$^6$ and R$^7$ are each independently selected from hydrogen or C$_1$–C$_6$-alkyl; and n is 0, 1 or 2.

8. A compound of claim 7, selected from the group consisting of

2-[6-(3-fluoro-benzyloxy)-1-oxo-3,4-dihydro-1H-isoquinolin-2-yl]-acetamide,

2-[6-(3-fluoro-benzyloxy)-1-oxo-3,4-dihydro-1H-isoquinolin-2-yl]-propionamide

2-[6-(4-fluoro-benzyloxy)-1-oxo-3,4-dihydro-1H-isoquinolin-2-yl]-propionamide,

2-[6-(3,4-difluoro-benzyloxy)-1-oxo-3,4-dihydro-1H-isoquinolin-2-yl]-propionamide, and 2-[6-(3-fluoro-benzyloxy)-1-oxo-3,4-dihydro-1H-isoquinolin-2-yl]-propionamide.

9. Enantiomers of compounds of formula I-A according to claim 7, which enantiomers are selected from the group consisting of 2-(R)-[6-(3-fluoro-benzyloxy)-1-oxo-3,4-dihydro-1H-isoquinolin-2-yl]-propionamide, 2-(R)-[6-(4-fluoro-benzyloxy)-1-oxo-3,4-dihydro-1H-isoquinolin-2-yl]-propionamide, 2-(S)-[6-(4-fluoro-benzyloxy)-1-oxo-3,4-dihydro-1H-isoquinolin-2-yl]-propionamide, 2-(S)-[6-(4-fluoro-benzyloxy)-1-oxo-3,4-dihydro-1H-isoquinolin-2-yl]-3-hydroxy-propionamide, and 2-(R)-[6-(2,6-difluoro-benzyloxy)-1-oxo-3,4-dihydro-1H-isoquinolin-2-yl]-propionamide.

10. A compound of formula

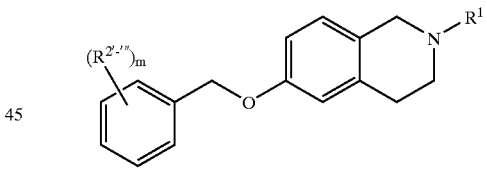

I-B wherein

R$^1$ is hydrogen or is a group of formula

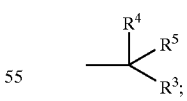

(a)

R$^{2^{1\text{-}111}}$ each R$^2$ is independently selected from halogen, halogen-(C$_1$–C$_6$)-alkyl, cyano, C$_1$–C$_6$-alkoxy or halogen-(C$_1$–C$_6$)-alkoxy, R$^3$ is selected from —(CH$_2$)$_n$—CO—NR$^6$R$^7$,
—(CH$_2$)$_n$—CN,
—(CH$_2$)$_p$—OR$^8$,
—(CH$_2$)$_n$—NR$^6$R$^7$,
—(CH$_2$)$_n$—CF$_3$,
—(CH$_2$)$_n$—NH—COR$^9$,
—(CH$_2$)$_n$-tetrahydrofuranyl, —(CH$_2$)$_p$—SR$^8$,
—(CH$_2$)$_p$—SO—R$^9$, or
—(CH$_2$)$_n$—CS—NR$^5$R$^6$;

R$^4$ is hydrogen, C$_1$–C$_6$-alkyl, CH$_2$)$_p$—OR$^8$, —(CH$_2$)$_p$—SR$^8$, or benzyl;

R$^5$ is hydrogen, C$_1$–C$_6$-alkyl, CH$_2$)$_p$—OR$^8$, —(CH$_2$)$_p$—SR$^8$, or benzyl;

R$^6$ and R$^7$ are each independently selected from hydrogen or C$_1$–C$_6$-alkyl;

R$^8$ is hydrogen or C$_1$–C$_6$-alkyl;

R$^9$ is C$_1$–C$_6$-alkyl;

m is 1, 2 or 3;

n is 0, 1 or 2; and p is 1 or 2;

or the pharmaceutically acceptable salts thereof.

11. The compound of claim 10, wherein R$^1$ is a group of formula (a); R$^3$ is —(CH$_2$)$_n$—CO—NR$^6$R$^7$, —(CH$_2$)$_n$—CN, —(CH$_2$)$_n$—CF$_3$, —(CH$_2$)$_p$—OR$^8$ or —(CH$_2$)$_n$-tetrahydrofuranyl; R$^6$ and R$^7$ are each independently selected from hydrogen or C$_1$–C$_6$-alkyl; R$^8$ is hydrogen or C$_1$–C$_6$-alkyl; n is 0, 1 or 2; and p is 1 or 2.

12. The compound of claim 11, wherein R$^3$ is —(CH$_2$)$_n$—CO—NR$^6$R$^7$; R$^6$ and R$^7$ are each independently selected from hydrogen or C$_1$–C$_6$-alkyl; and n is 0, 1 or 2.

13. A compound of formula I-B according to claim 12, that is selected from the group consisting of 2-[6-(3-fluoro-benzyloxy)3,4-dihydro-1H-isoquinolin-2-yl]-propionamide, 2-[6-(4-fluoro-benzyloxy)3,4-dihydro-1H-isoquinolin-2-yl]-acetamide, 2-[6-(3-fluoro-benzyloxy)-3,4-dihydro-1H-isoquinolin-2-yl]-acetamide, and 2-[6-(4-fluoro-benzyloxy)3,4-dihydro-1H-isoquinolin-2-yl]-propionamide.

14. The compound of formula I-B according to claim 11, wherein R$^3$ is —(CH$_2$)$_p$—OR$^8$; R$^8$ is C$_1$–C$_6$-alkyl; and p is 1 or 2.

15. A compound of formula

I-C

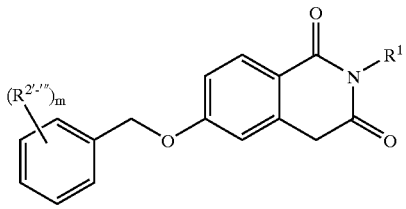

wherein

R$^1$ is hydrogen or is a group of formula (a)

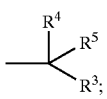

R$^{2^{1-111}}$ is independently selected from halogen, halogen-(C$_1$–C$_6$)-alkyl, cyano, C$_1$–C$_6$-alkoxy or halogen-(C$_1$–C$_6$)-alkoxy, R$^3$ is selected from —(CH$_2$)$_n$—CO—NR$^6$R$^7$,
—(CH$_2$)$_n$—CN,
—(CH$_2$)$_p$—OR$^8$,
—(CH$_2$)$_n$—NR$^6$R$^7$,
—(CH$_2$)$_n$—CF$_3$,
—(CH$_2$)$_n$—NH—COR$^9$,
—(CH$_2$)$_n$-tetrahydrofuranyl,
—(CH$_2$)$_p$—SR$^8$,
—(CH$_2$)$_p$—SO—R$^9$, or
—(CH$_2$)$_n$—CS—NR$^5$R$^6$;

R$^4$ is hydrogen, C$_1$–C$_6$-alkyl, —(CH$_2$)$_p$—OR$^8$, —(CH$_2$)$_p$—SR$^8$, or benzyl;

R$^5$ is hydrogen, C$_1$–C$_6$-alkyl, —(CH$_2$)$_p$—OR$^8$, —(CH$_2$)$_p$—SR$^8$, or benzyl;

R$^6$ and R$^7$ are each independently selected from hydrogen or C$_1$–C$_6$-alkyl;

R$^8$ is hydrogen or C$_1$–C$_6$-alkyl;

R$^9$ is C$_1$–C$_6$-alkyl;

m is 1, 2 or 3;

n is 0, 1 or 2; and p is 1 or 2;

or the pharmaceutically acceptable salts thereof.

16. The compound of claim 15, wherein R$^3$ is –(CH$_2$)$_n$—CO—NR$^6$R$^7$; R$^6$ and R$^7$ are each independently selected from hydrogen or C$_1$–C$_6$-alkyl; and n is 0, 1 or 2.

17. A compound of claim 16 that is selected from the group consisting of 2-(R)-[6-(4-fluoro-benzyloxy)-1,3-dioxo-3,4-dihydro-1H-isoquinolin-2-yl]-propionamide, and 2-(S)-[6-(4-fluoro-benzyloxy)-1,3-dioxo-3,4-dihydro-1H-isoquinolin-2-yl]-propionamide.

18. A compound of formula

I-D

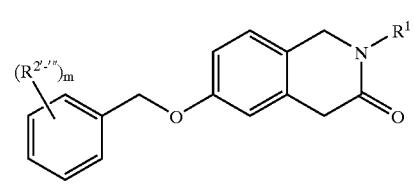

wherein

R$^1$ is hydrogen or is a group of formula (a)

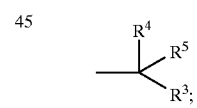

R$^{2^{1-111}}$ each R$^2$ is independently selected from halogen, halogen-(C$_1$–C$_6$)-alkyl, cyano, C$_1$–C$_6$-alkoxy or halogen-(C$_1$–C$_6$)-alkoxy, R$^3$ is selected from —(CH$_2$)$_n$—CO—NR$^6$R$^7$,
—(CH$_2$)$_n$—CN,
—(CH$_2$)$_p$—OR$^8$,
—(CH$_2$)$_n$—NR$^6$R$^7$,
—(CH$_2$)$_n$—CF$_3$,
—(CH$_2$)$_n$—NH—COR$^9$,
—(CH$_2$)$_n$-tetrahydrofuranyl,
—(CH$_2$)$_p$—SR$^8$,
—(CH$_2$)$_p$—SO—R$^9$, or
—(CH$_2$)$_n$—CS—NR$^5$R$^6$;

R$^4$ is hydrogen, C$_1$–C$_6$-alkyl, —(CH$_2$)$_p$—OR$^8$, —(CH$_2$)$_p$—SR$^8$, or benzyl;

R$^5$ is hydrogen, C$_1$–C$_6$-alkyl, —(CH$_2$)$_p$—OR$^8$, —(CH$_2$)$_p$—SR$^8$, or benzyl;

$R^6$ and $R^7$ are each independently selected from hydrogen or $C_1$–$C_6$-alkyl;

$R^8$ is hydrogen or $C_1$–$C_6$-alkyl;

$R^9$ is $C_1$–$C_6$-alkyl;

m is 1, 2 or 3;

n is 0, 1 or 2; and p is 1 or 2;

or the pharmaceutically acceptable salts thereof.

19. The compound claim 15, wherein $R^3$ is —$(CH_2)_n$—CO—$NR^6R^7$; $R^6$ and $R^7$ are each independently selected from hydrogen or $C_1$–$C_6$-alkyl; and n is 0, 1 or 2.

20. A compound of claim 19, that is selected from the group consisting of 2-(S)-[6 (4-fluoro-benzyloxy)-3-oxo-3,4-dihydro-1H-isoquinolin-2-yl]-propionamide, and 2(R)-[6-(4-fluoro-benzyloxy)-3-oxo-3,4-dihydro-1H-isoquinolin-2-yl]-propionamide.

21. A process for the preparation of a compound of claim 1 comprising:

a) reacting a compound of formula

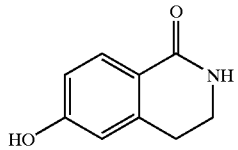

II with a compound of formula

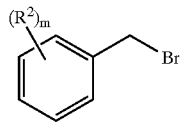

III to obtain a compound of formula

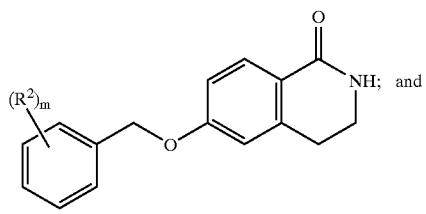

I-A$_1$ (b) reacting the compound of formula I-A$_1$, with a compound of formula

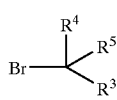

IV to obtain a compound of formula

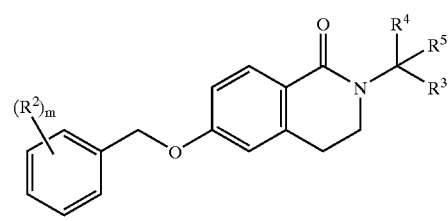

I-A$_2$

22. A process for the preparation of a compound of claim 1 comprising:

a) reducing a compound of formula

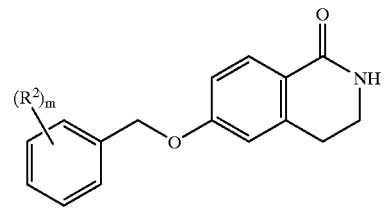

I-A$_1$ to obtain a compound of formula

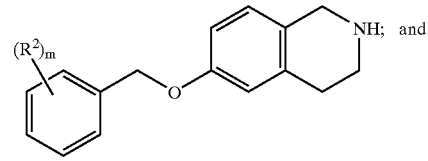

I-B$_1$; and b) reacting the compound of formula I-B$_1$, with a compound of formula

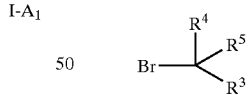

IV to obtain a compound of formula

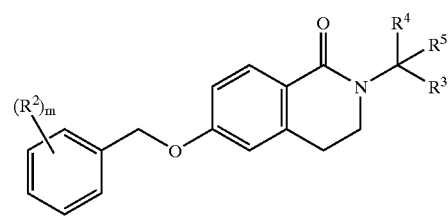

I-B$_2$

23. A process for the preparation of a compound of claim 1 comprising:

a) reacting a compound of formula

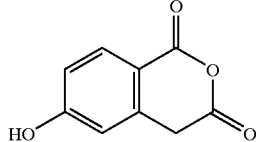

V with a compound of formula

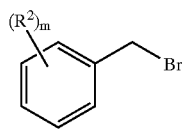

III to obtain a compound of formula

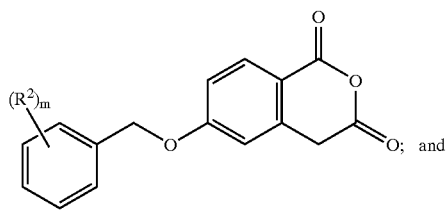

VI b) reacting the compound of formula VI with a compound of formula

  H$_2$N—R$^1$

VII to obtain a compound of formula

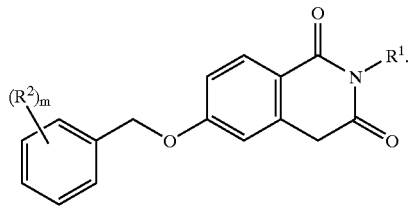

I-C

24. A process for the preparation of a compound of claim 1 comprising:

a) oxidizing of a compound of formula

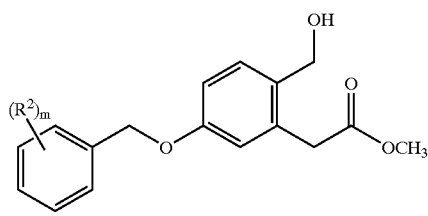

IX to the corresponding aldehyde of formula

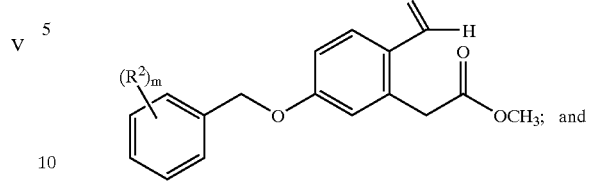

IXa b) reacting the compound of formula IXa in the presence of an reducing agent with a compound of formula

H$_2$N—R$^1$

VII to obtain a compound of formula

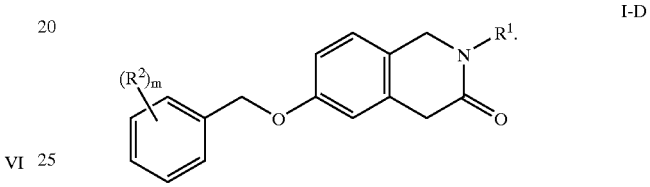

I-D

25. A process for the preparation of an enantiomer of a compound of claim 1 comprising:

a) reacting a compound of formula

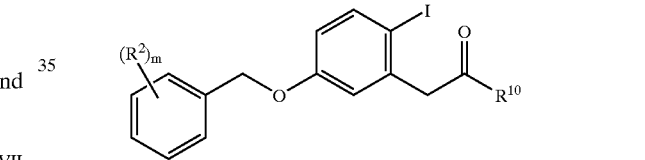

X wherein R$^{10}$ is hydrogen or hydroxy, with an optically active amino derivative of formula

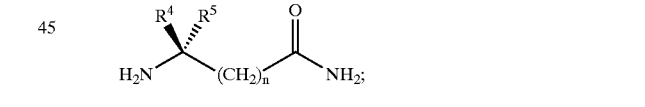

XI b) reducing the resulting compound to obtain a compound of formula

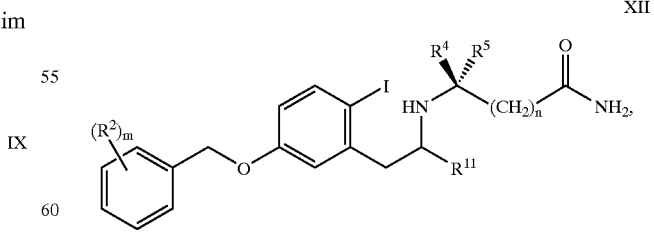

XII wherein R$^{11}$ is hydrogen or oxo; and c) reacting the resulting compound with carbon monoxide under pressure in
the presence of a palladium (II) salt to obtain a compound of formula

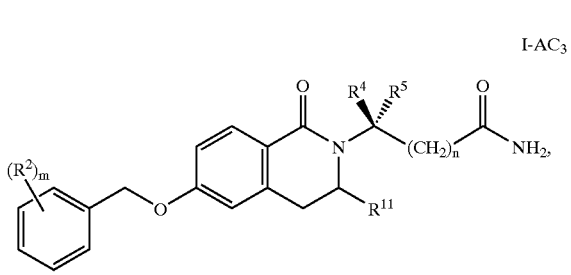

wherein R¹¹ is hydrogen or oxo.

26. A pharmaceutical composition comprising a therapeutically effective amount of a compound of claim 1 and a pharmaceutically acceptable carrier and/or excipient.

27. A compound of formula

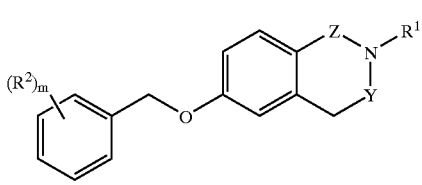

wherein
Y is >C=O or —CH$_2$—;
Z is >C=O or —CH$_2$—;
R¹ is hydrogen or is a group of formula

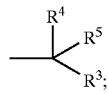

R³ is selected from —(CH$_2$)$_n$—CO—NR⁶R⁷,
—(CH$_2$)$_n$—CN,
—(CH$_2$)$_p$—OR⁸,
—(CH$_2$)$_n$—NR⁶R⁷,
—(CH$_2$)$_n$—CF$_3$,
—(CH$_2$)$_n$—NH—COR⁹,
—(CH$_2$)$_n$-tetrahydrofuranyl,
—(CH$_2$)$_p$—SR⁸,
—(CH$_2$)$_p$—SO—R⁹, or
—(CH$_2$)$_n$—CS—NR⁵R⁶;
R⁴ is hydrogen, C$_1$–C$_6$-alkyl, —(CH$_2$)$_p$—OR⁸, —(CH$_2$)$_p$—SR⁸, or benzyl;
R⁵ is hydrogen, C$_1$–C$_6$-alkyl, —(CH$_2$)$_p$—OR⁸, —(CH$_2$)$_p$—SR⁸, or benzyl;
R⁶ and R⁷ are each independently selected from hydrogen or C$_1$–C$_6$-alkyl;
R⁸ is hydrogen or C$_1$–C$_6$-alkyl;
R⁹ is C$_1$–C$_6$-alkyl;
m is 1, 2 or 3;
n is 0, 1 or 2; and
p is 1 or 2;
R² is halogen, halogen-(C$_1$–C$_6$)-alkyl, cyano, C$_1$–C$_6$-alkoxy or halogen-(C$_1$–C$_6$)alkoxy;
or the pharmaceutically acceptable salts thereof.

28. A compound of claim 1, wherein R³ is —CH$_2$)$_n$—CO—NR⁶R⁷.

29. A compound of claim 1, selected from the group consisting of

2-[1-oxo-6-(4-trifluoromethyl-benzyloxy)-3,4-dihydro-1H-isoquinolin-2-yl]-propionamide;
2-[6-(2-Fluoro-benzyloxy)-1-oxo-3,4-dihydro-1H-isoquinolin-2-yl]-propionamide;
2(R)-[6-(2,6-Difluoro-benzyloxy)-1-oxo-3,4-dihydro-1H-isoquinolin-2-yl]-propionamide;
2(R)-[6-(2-Fluoro-benzyloxy)-1-oxo-3,4-dihydro-1H-isoquinolin-2-yl]-propionamide;
2(R)[6-(2,3-Difluoro-benzyloxy)-1-oxo-3,4-dihydro-1H-isoquinolin-2-yl]-propionamide;
2(R)[6-(3-Fluoro-benzyloxy)-1-oxo-3,4-dihydro-1H-isoquinolin-2-yl]-propionamide;
2(S)-[6-(3-Fluoro-benzyloxy)-1-oxo-3,4-dihydro-1H-isoquinolin-2-yl]-propionamide; and
2(S)-[6-(3,4-Difluoro-benzyloxy)-1-oxo-3,4-dihydro-1H-isoquinolin-2-yl]-propionamide.

30. A compound of claim 1, selected from the group consisting of
6-(3-Fluoro-benzyloxy)-3,4-dihydro-2H-isoquinolin-1-one;
2-[6-(4-Fluoro-benzyloxy)-1-oxo-3,4-dihydro-1H-isoquinolin-2-yl]-acetamide;
2(R)-[6-(3-Cyano-benzyloxy)-1-oxo-3,4-dihydro-1H-isoquinolin-2-yl]-propionamide;
2(R)-[6-(3,5-Difluoro-benzyloxy)-1-oxo-3,4-dihydro-1H-isoquinolin-2-yl]-propionamide;
3-[6-(4-Fluoro-benzyloxy)-3,4-dihydro-1H-isoquinolin-2-yl]-propionamide;
3-[6-(3-Fluoro-benzyloxy)-3,4-dihydro-1H-isoquinolin-2-yl]-propionamide;
2(R)-[(3,4-Difluoro-benzyloxy)-1-oxo-3,4-dihydro-1H-isoquinolin-2-yl]-propionamide; and
2-[6-(3-Chloro-benzyloxy)-1-oxo-3,4-dihydro-1H-isoquinolin-2-yl]-propionamide.

31. A compound of claim 1, selected from the group consisting of
3-[6-(3-Fluoro-benzyloxy)-1-oxo-3,4-dihydro-1H-isoquinolin-2-yl]-propionamide;
2-(S)-[6-(4-Fluoro-benzyloxy)-1-oxo-3,4-dihydro-1H-isoquinolin-2-yl]-4-methylsulfanyl-butyramide;
2-(R)-[6-(4-Fluoro-benzyloxy)-1-oxo-3,4-dihydro-1H-isoquinolin-2-yl]-3-hydroxy-propionamide;
2-(S)-[6-(4-Fluoro-benzyloxy)-1-oxo-3,4-dihydro-1H-isoquinolin-2-yl]-4-methyl-pentanoic acid amide;
2-(S)-[6-(4-Fluoro-benzyloxy)-1-oxo-3,4-dihydro-1H-isoquinolin-2-yl]-butyramide;
2-(R)-[6-(4-Fluoro-benzyloxy)-1-oxo-3,4-dihydro-H-isoquinolin-2-yl]-3-phenyl-propionamide;
2-(S)-[6-(4-Fluoro-benzyloxy)-1-oxo-3,4-dihydro-1H-isoquinolin-2-yl]-3-methyl-butyramide;
2-(S)-[6-(4-Fluoro-benzyloxy)-1-oxo-3,4-dihydro-1H-isoquinolin-2-yl]-3-phenyl-propionamide; and
2-[6-(4-Fluoro-benzyloxy)-1-oxo-3,4-dihydro-1H-isoquinolin-2-yl]-isobutyramide.

32. A compound of claim 1, selected from the group consisting of
6-(3-Fluoro-benzyloxy)-2-(2-hydroxy-1-methyl-ethyl)-3,4-dihydro-2H-isoquinolin-1-one;
6-(3-Fluoro-benzyloxy)-2-(2-hydroxy-ethyl)-3,4-dihydro-2H-isoquinolin-1-one;
6-(3-Fluoro-benzyloxy)-2-(2-methoxy-1-methyl-ethyl)-3,4-dihydro-2H-isoquinolin-1-one;
6-(3-Fluoro-benzyloxy)-2-(2-methoxy-ethyl)-3,4-dihydro-2H-isoquinolin-1-one;
2-(2-Ethoxy-ethyl)-6-(3-fluoro-benzyloxy)-1,2,3,4-tetrahydro-isoquinoline;

6-(4-Fluoro-benzyloxy)-2-(2-methoxy-ethyl)-1,2,3,4-tetrahydro-isoquinoline; and 2-(2-Ethoxy-ethyl)-6-(4-fluoro-benzyloxy)-1,2,3,4-tetrahydro-isoquinoline.

33. A compound of claim 1, which is selected from the group consisting of

[6-(3-Fluoro-benzyloxy)-1-oxo-3,4-dihydro-1H-isoquinolin-2-yl]-acetonitrile;

3-[6-(3-Fluoro-benzyloxy)-1-oxo-3,4-dihydro-1H-isoquinolin-2-yl]-propionitrile;

6-(4-Fluoro-benzyloxy)-2-(4,4,4-trifluoro-butyl)-1,2,3,4-tetrahydro-isoquinoline; and 6-(4-Fluoro-benzyloxy)-2-(tetrahydro-furan-2-ylmethyl)-1,2,3,4-tetrahydro-isoquinoline.

34. A compound of claim 1, which is 2-[6 (4-Fluoro-benzyloxy)-1-oxo-3,4-dihydro-1H-isoquinolin-2-yl]-propionamide.

35. A compound of claim 1, which is 2-(R)-[6-(3-Fluoro-benzyloxy)-1-oxy-3,4-dihydro-1H-isoquinolin-2-yl]-propionamide.

36. A compound of claim 1, which is 2(R)-[6-(4-Fluoro-benzyloxy)-1-oxo-3,4-dihydro-1H-isoquinolin-2-yl]-propionamide.

37. A compound of claim 1, which is 2 (S)-[6-(4-Fluoro-benzyloxy)-1-oxo-3,4-dihydro-1H-isoquinolin-2-yl]-propionamide.

\* \* \* \* \*

UNITED STATES PATENT AND TRADEMARK OFFICE
CERTIFICATE OF CORRECTION

PATENT NO. : 6,818,774 B2
APPLICATION NO. : 10/417378
DATED : November 16, 2004
INVENTOR(S) : Cesura et al.

It is certified that error appears in the above-identified patent and that said Letters Patent is hereby corrected as shown below:

Claim 8, Column 54, lines 20 and 21:

"2-[6-(4-fluoro-benzyloxy)-1-oxo-3,4-dihydro-1H-isoquinolin-2-yl]-propionamide," should read -- 2-[6-(4-fluoro-benzyloxy)-1-oxo-3,4-dihydro-1H-isoquinolin-2-yl]-propionamide, and --.

Claim 8, Column 54, lines 22 and 23:

"2-[6-(3,4-difluoro-benzyloxy)-1-oxo-3,4-dihydro-1H-isoquinolin-2-yl]-propionamide, and" should read -- 2-[6-(3,4-difluoro-benzyloxy)-1-oxo-3,4-dihydro-1H-isoquinolin-2-yl]-propionamide. --.

Claim 8, Column 54, lines 24 and 25:

"2-[6-(3-fluoro-benzyloxy)-1-oxo-3,4-dihydro-1H-isoquinolin-2-yl]-propionamide." Should be deleted in its entirety.

Signed and Sealed this

Nineteenth Day of December, 2006

JON W. DUDAS
*Director of the United States Patent and Trademark Office*